(12) United States Patent
Davies et al.

(10) Patent No.: US 8,975,428 B2
(45) Date of Patent: Mar. 10, 2015

(54) DIRHODIUM CATALYST COMPOSITIONS AND SYNTHETIC PROCESSES RELATED THERETO

(75) Inventors: Huw M. L. Davies, Duluth, GA (US);
Jørn H. Hansen, Atlanta, GA (US);
Changming Qin, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/123,389

(22) PCT Filed: Jun. 1, 2012

(86) PCT No.: PCT/US2012/040608
§ 371 (c)(1),
(2), (4) Date: Feb. 17, 2014

(87) PCT Pub. No.: WO2012/167198
PCT Pub. Date: Dec. 6, 2012

(65) Prior Publication Data
US 2014/0155643 A1 Jun. 5, 2014

(51) Int. Cl.
*C07F 15/00* (2006.01)
*B01J 31/00* (2006.01)
*B01J 31/22* (2006.01)

(52) U.S. Cl.
CPC .......... *C07F 15/0073* (2013.01); *C07F 15/008* (2013.01); *B01J 31/2239* (2013.01); *B01J 2531/0219* (2013.01); *B01J 2531/822* (2013.01); *B01J 2231/325* (2013.01)
USPC .......................................... 556/136; 502/150

(58) Field of Classification Search
CPC  C07F 15/0073; C07F 15/008; B01J 31/2239; B01J 2231/325; B01J 2531/0219; B01J 2531/822

USPC .......................................... 556/136; 502/150
See application file for complete search history.

(56) References Cited

U.S. PATENT DOCUMENTS

| 5,789,333 A | 8/1998 | Angelici |
| 6,762,304 B2 | 7/2004 | Davies |
| 7,385,064 B1 | 6/2008 | Davies et al. |

FOREIGN PATENT DOCUMENTS

| EA | 013125 B1 | 2/2010 |
| SU | 319336 A1 | 12/1971 |
| WO | 03018184 A2 | 3/2003 |

OTHER PUBLICATIONS

A.R. de Souza et al., Thermochimica Acta, vol. 343, pp. 119-125 (2000).*
Davies et al., Asymmetric Cyclopropanations by Rhodium(II) N-(Arylsulfonyl)prolinate Catalyzed Decomposition of Vinyldiazomethanes in the Presence of Alkenes. Practical Enantioselective Synthesis of the Four Stereoisomers of 2-Phenylcyclopropan-1-amino Acid, JACS, 1996, 6897-6907, 118.

(Continued)

*Primary Examiner* — Porfirio Nazario Gonzalez
(74) *Attorney, Agent, or Firm* — Emory Patent Group

(57) ABSTRACT

This disclosure relates to compositions comprising dirhodium catalysts and uses related thereto, e.g., in enantioselective transformations of donor/acceptor carbenoids. In certain embodiments, the dirhodium catalyst comprises a cyclopropyl ring substituted with a carboxylic acid ligand. In certain embodiments, the disclosure relates to compositions comprising a compound of the following formula, or salts thereof wherein, $R^1$, $R^2$, and $R^3$ are defined herein.

20 Claims, 6 Drawing Sheets

(56) References Cited

OTHER PUBLICATIONS

De Souza et al., Thermal behaviour of some rhodium(II) cycloalkanocarboxylate complexes, Thermochimica Acta, 2000, 119-125, 343.

Davies & Qin, Role of Sterically Demanding Chiral Dirhodium Catalysts in Site-, Selective C—H Functionalization of Activated Primary C—H Bonds, JACS, 2014, 9792-9796, 136.

Davies & Manning, Catalytic C—H functionalization by metal carbenoid and nitrenoid insertion, Nature, 2008, 417-424, 451.

Davies & Denton, Application of donor/acceptor-carbenoids to the synthesis of natural products, Chem. Soc. Rev., 2009, 3061-3071, .38.

Davies, et al., Combined C—H Activation/Cope Rearrangement as a Strategic Reaction in Organic Synthesis: Total Synthesis of (−)-Colombiasin A and (−)-Elisapterosin B, J. Am. Chem. Soc., 2006, 2485-2490, 128.

Davies & Walji, Direct Synthesis of (+)-Erogorgiaene through a Kinetic Enantiodifferentiating Step, Angew. Chem., Int. Ed., 2005, 1733-1735, 44.

Davies et al., Tandem Asymmetric Cyclopropanation/Cope Rearrangement. A Highly Diastereoselective and Enantioselective Method for the Construction of 1,4-Cycloheptadienes, J. Am. Chem. Soc. 1998, 3326-3331, 120.

Reddy & Davies, Asymmetric Synthesis of Tropanes by Rhodium-Catalyzed [4+3] Cycloaddition, J. Am. Chem. Soc., 2007, 10312-10313, 129.

Davies & Morton, Guiding principles for site selective and stereoselective intermolecular C—H functionalization by donor/acceptor rhodium carbenes, Chem. Soc. Rev., 2011, 1857-1869, 40.

Reddy & Davies, Dirhodium Tetracarboxylates Derived from Adamantylglycine as Chiral Catalysts for Enantioselective C—H Aminations, Org. Lett., 2006, 5013-5016, 8.

Davies et al., Guide to enantioselective dirhodium(II)-catalyzed cyclopropanation with aryldiazoacetates, Tetrahedron, 2013, 5765-5771, 69.

Davies et al., Rhodium-catalyzed enantioselective cyclopropanation of electron-deficient alkenes, Chem. Sci., 2013, 2844-2850, 4.

Davies et al., D2-Symmetric Dirhodium Catalyst Derived from a 1,2,2-Triarylcyclopropanecarboxylate Ligand: Design, Synthesis and Application, JACS, 2011, 19198-19204, 133.

Davies et al., Silica-Immobilized Chiral Dirhodium(II) Catalyst for Enantioselective Carbenoid Reactions, Organic Letters, 2013, 6136-6139, 15.

\* cited by examiner

DIRHODIUM CATALYST COMPOSITIONS AND SYNTHETIC PROCESSES RELATED THERETO

STATEMENT REGARDING FEDERALLY FUNDED RESEARCH

This invention was made with government support under Grants CHE 0750273 awarded by the National Science Foundation. The government has certain rights in the invention.

CROSS REFERENCE TO RELATED APPLICATIONS

This application claims priority to U.S. provisional application No. 61/492,834 filed Jun. 3, 2011, hereby incorporated by reference in its entirety.

BACKGROUND

Dirhodium catalysts have played a prominent role in the metal-catalyzed reactions of diazo compounds. Effort has been made to prepare various chiral dirhodium tetracarboxylate and dirhodium tetracarboxamidate catalysts. A series of prolinate-based dirhodium catalysts, such as $Rh_2(S\text{-}DOSP)_4$ (See FIG. 1, compound 1), have been prepared and examined for their capacity to induce asymmetric induction in the reactions of donor/acceptor carbenoids. See Davies et al., JACS, 1996, 118:6897-6907. The asymmetric induction in these catalyzed reactions is sensitive to solvent and substrate structure. Asymmetric induction with $Rh_2(S\text{-}DOSP)_4$ as catalyst requires the use of a methyl ester as the acceptor group in the carbenoid and nonpolar solvents such as hydrocarbons. The phthalimidocarboxylate $Rh_2(S\text{-}PTAD)_4$ (See FIG. 1, compound 2) and the bridged dicarboxylate catalyst, $Rh_2(S\text{-}biTISP)_2$ (See FIG. 1, compound 3) may be prepared by relatively tedious synthetic routes. Thus, there is a need for improved catalysts.

SUMMARY

This disclosure relates to compositions comprising dirhodium catalysts and uses related thereto, e.g., in enantioselective transformations of donor/acceptor carbenoids. In certain embodiments, the dirhodium catalyst comprises a cyclopropyl ring substituted with a carboxylic acid ligand. In certain embodiments, the disclosure relates to compositions comprising a compound of the following formula,

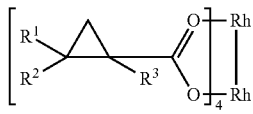

or derivatives or salts thereof wherein, $R^1$, $R^2$, and $R^3$ are defined herein.

In certain embodiments, the disclosure relates to compositions comprising $Rh_2(S\text{-}biTISP)_2$, $Rh_2(R\text{-}biTISP)_2$, or a compound of formula

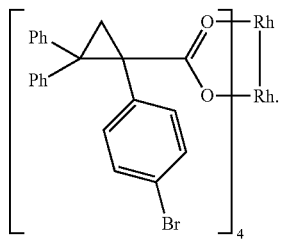

In certain embodiments, the disclosure relates to methods of preparing dirhodium catalysts or intermediates disclosed herein by mixing starting materials with catalysts under conditions such that the catalysts or intermediates are formed.

In certain embodiments, the disclosure contemplates enantioselective reactions of donor/acceptor carbenoids, such as cyclopropanations, formal [4+3] cycloadditions, C—H functionalizations, and ylide transformations comprising mixing a compound comprising a carbenoid precursor, e.g., a diazo compound, and catalysts disclosed herein and reactive compounds under conditions such that a synthetic compound is formed.

DETAILED DESCRIPTION

Terms

Figure 1:
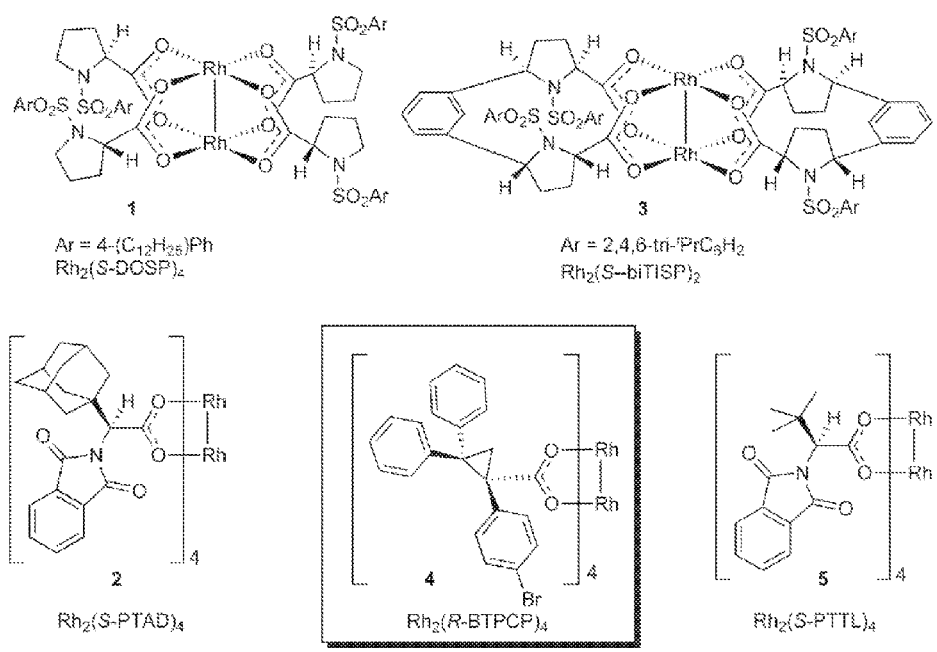
FIG. 1 illustrates certain chiral dirhodium catalysts.

Unless defined otherwise, all technical and scientific terms used herein have the same meaning as is commonly understood by one of skill in the art. The following definitions are provided to help interpret the disclosure and claims of this application. In the event a definition in this section is not consistent with definitions elsewhere, the definition set forth in this section will control.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxy group. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze, hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)$_2$Ra, —OS(=O)2Ra and —S(=O) 2ORa. Ra and Rb in this context may be the same or different and independently hydrogen, halogen hydroxy, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

When used in reference to compound(s) disclosed herein, "salts" refer to derivatives of the disclosed compound(s) where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH$_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—CH$_3$).

"Alkanoyl" refers to an alkyl as defined above attached through a carbonyl bridge (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfamoyl" refers to an alkyl as defined above attached through a sulfamoyl bridge (i.e., —S(=O)$_2$NHalkyl), and an "Arylsulfamoyl" refers to an alkyl attached through a sulfamoyl bridge (i.e., —S(=O)$_2$NHaryl).

"Alkylsulfinyl" refers to an alkyl as defined above with the indicated number of carbon atoms attached through a sulfinyl bridge (i.e. —S(=O)alkyl).

The terms "halogen" and "halo" refer to fluorine, chlorine, bromine, and iodine.

Dirhodium Catalysts

In certain embodiments, the disclosure relates to a dirhodium catalyst comprising a cyclopropyl ring substituted with a carboxylic acid ligand. In certain embodiments, the disclosure relates to compositions comprising a compound of the following formula,

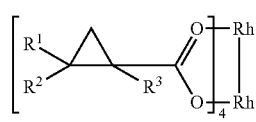

or salts thereof wherein,

R¹ is hydrogen, alkyl, halogen, cyano, hydroxy, amino, mercapto, formyl, carboxy, carbamoyl, alkoxy, alkanoyl, alkylthio, alkylamino, (alkyl)₂amino, alkylsulfinyl, alkylsulfonyl, arylsulfonyl, carbocyclyl, aryl, or heterocyclyl, wherein R¹ is optionally substituted with one or more, the same or different, R⁴;

R² is hydrogen, alkyl, halogen, cyano, hydroxy, amino, mercapto, formyl, carboxy, carbamoyl, alkoxy, alkanoyl, alkylthio, alkylamino, (alkyl)₂amino, alkylsulfinyl, alkylsulfonyl, arylsulfonyl, carbocyclyl, aryl, or heterocyclyl, wherein R² is optionally substituted with one or more, the same or different, R⁴;

R³ is hydrogen, alkyl, halogen, cyano, hydroxy, amino, mercapto, formyl, carboxy, carbamoyl, alkoxy, alkanoyl, alkylthio, alkylamino, (alkyl)₂amino, alkylsulfinyl, alkylsulfonyl, arylsulfonyl, carbocyclyl, aryl, or heterocyclyl, wherein R³ is optionally substituted with one or more, the same or different, R⁴;

R⁴ is alkyl, halogen, cyano, hydroxy, amino, mercapto, formyl, carboxy, carbamoyl, alkoxy, alkanoyl, alkylthio, alkylamino, (alkyl)₂amino, alkylsulfinyl, alkylsulfonyl, arylsulfonyl, carbocyclyl, aryl, or heterocyclyl, wherein R⁴ is optionally substituted with one or more, the same or different, R⁵;

R⁵ is alkyl, halogen, cyano, hydroxy, amino, mercapto, formyl, carboxy, carbamoyl, alkoxy, alkanoyl, alkylthio, alkylamino, (alkyl)₂amino, alkylsulfinyl, alkylsulfonyl, arylsulfonyl, carbocyclyl, aryl, or heterocyclyl, wherein R⁵ is optionally substituted with one or more, the same or different, R⁶; and R⁶ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the catalyst is in a composition with greater than 55%, 75%, 85%, 95%, 98%, or 99% enantiomeric excess of the following stereioisomers:

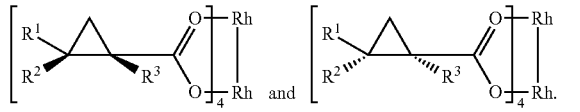

In certain embodiments, R¹ is carbocyclyl, aryl, or heterocyclyl.

In certain embodiments, R¹ is an aryl or an aromatic heterocyclyl.

In certain embodiments, R¹ is a phenyl optionally substituted with one or more R⁴.

In certain embodiments, R¹ is a phenyl optionally substituted with one or more halogen, alkyl, or alkoxy.

In certain embodiments, R¹ is hydrogen.

In certain embodiments, R² is carbocyclyl, aryl, or heterocyclyl.

In certain embodiments, R² is an aryl or an aromatic heterocyclyl.

In certain embodiments, R² is a phenyl optionally substituted with one or more R⁴.

In certain embodiments, R² is a phenyl optionally substituted with one or more halogen, alkyl, or alkoxy.

In certain embodiments, R³ is carbocyclyl, aryl, or heterocyclyl.

In certain embodiments, R³ is an aryl or an aromatic heterocyclyl.

In certain embodiments, R³ is a phenyl optionally substituted with one or more R⁴.

In certain embodiments, R³ is a phenyl optionally substituted with one or more halogen, alkyl, or alkoxy.

In certain embodiments, R³ is a phenyl substituted with a halogen.

In certain embodiments, R³ is a phenyl substituted with a halogen in the otho or para position.

In certain embodiments, the disclosure relates to compositions comprising a compound,

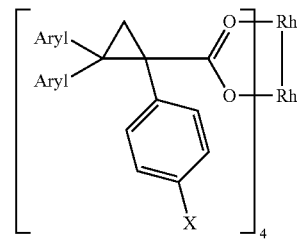

wherein X is an electron withdrawing group.

In certain embodiments, the catalyst is in a composition with greater than 55%, 75%, 85%, 95%, 98%, or 99% enantiomeric excess of the following stereioisomers:

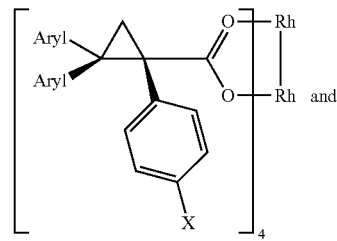

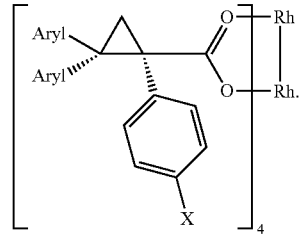

In certain embodiments, X is a halogen.

In certain embodiments, the disclosure relates to compositions comprising a compound

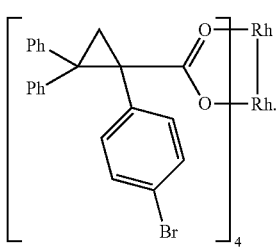

In certain embodiments, the catalyst is in a composition with greater than 55%, 75%, 85%, 95%, 98%, or 99% enantiomeric excess of the following stereoisomers:

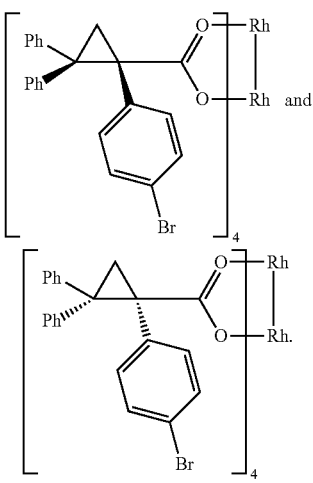

Synthetic Processes

Many enantioselective reactions of donor/acceptor carbenoids may be utilized with dirhodium catalysts disclosed herein. In certain embodiments, the dirhodium can be used to make intermediates for pharmaceutical agents as exemplified herein. See Davies & Manning, Nature, 2008, 451, 417-424; Davies & Denton, Chem. Soc. Rev., 2009, 38, 3061-3071; Davies, et al., J. Am. Chem. Soc., 2006, 128, 2485-2490; and Davies &. Walji, Angew. Chem., Int. Ed., 2005, 44, 1733-1735, all hereby incorporated by reference.

In certain embodiments, the disclosure contemplates reactions of donor/acceptor carbenoids, such as cyclopropanations, formal [4+3] cycloadditions, C—H functionalizations, and ylide transformations comprising mixing a compound comprising a carbenoid precursor, e.g., a diazo compound, and catalysts disclosed herein and reactive compounds under conditions such that a synthetic compound is formed.

In certain embodiments, the disclosure relates to methods of making a synthetic compound comprising mixing a) a diazo compound, b) a compound with a carbon hydrogen bond, and c) a dirhodium catalyst disclosed herein, under conditions such that a synthetic compound is formed comprising a carbon to carbon bond between the diazo compound and the compound with a carbon hydrogen bond. The synthetic compound may be the result of an inter or an intramolecular reaction.

In certain embodiments, the disclosure relates to methods of making a synthetic compound comprising mixing a) a diazo compound, b) a compound with a nitrogen hydrogen bond, and c) a dirhodium catalyst disclosed herein, under conditions such that a synthetic compound is formed comprising a carbon to nitrogen bond between the diazo compound and the compound with a nitrogen hydrogen bond. The synthetic compound may be the result of an inter or an intramolecular reaction.

In certain embodiments, the disclosure relates to cyclopropanation reactions using catalysts disclosed herein. See Davies et al., J. Am. Chem. Soc. 1996, 118, 6897-6907, hereby incorporated by reference. In certain embodiments, the disclosure relates to methods of making a synthetic compound comprising mixing a) a diazo compound such as vinyldiazomethane and vinyldiazoactates optionally substituted with one or more substituents, b) a double bond compound such as an alkene or diene optionally substituted with one or more substituent, and c) a compound comprising a dirhodium catalyst disclosed herein under conditions such that a synthetic compound is formed comprising a cyclopropyl ring and carbon to carbon bond between the diazo compound and the double bond compound.

In certain embodiments, the diazo compound has the following formula,

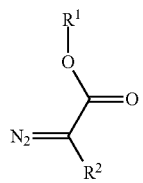

the double bond compound has the following formula,

and the synthetic compound has the following formula,

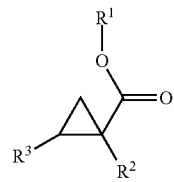

wherein, $R^1$ is alkyl, carbocyclyl, aryl, or heterocyclyl, wherein $R^1$ is optionally substituted with one or more, the same or different, $R^4$;

$R^2$ is alkyl, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^4$;

$R^3$ is hydrogen, alkyl, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^4$;

$R^4$ is alkyl, halogen, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$;

$R^5$ is alkyl, halogen, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$; and $R^6$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is alkyl optionally substituted with one or more, the same or different, $R^4$.

In certain embodiments, $R^2$ is an electron donating group selected from cyano, alkenyl, alkynyl, formyl, carbamoyl, carboxy, alkylsulfinyl, alkylsulfonyl, or arylsulfonyl, aryl, or an aromatic heterocyclyl optionally substituted with one or more, the same or different, $R^4$.

In certain embodiments, $R^2$ is aryl or an aromatic heterocyclyl optionally substituted with one or more, the same or different, $R^4$.

In certain embodiments, $R^3$ is an electron donating group selected from cyano, alkenyl, alkynyl, formyl, carbamoyl, carboxy, alkylsulfinyl, alkylsulfonyl, or arylsulfonyl, aryl, or an aromatic heterocyclyl optionally substituted with one or more, the same or different, $R^4$.

In certain embodiments, $R^3$ is aryl or an aromatic heterocyclyl optionally substituted with one or more, the same or different, $R^4$.

In certain embodiments, the synthetic product is in a composition with greater than 55%, 75%, 85%, 95%, 98%, or 99% enantiomeric excess of the following stereoisomers:

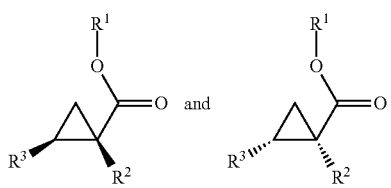

In certain embodiments, the diazo compound has the following formula,

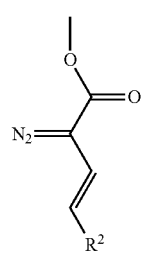

the double bond compound has the following formula,

and the synthetic compound has the following formula,

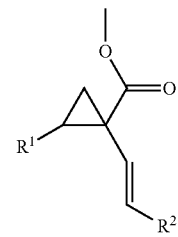

or salts thereof wherein
$R^1$ is phenyl optionally substituted with one or more substituent and
$R^2$ is phenyl optionally substituted with one or more substituent.

In certain embodiments, the synthetic product is in a composition with greater than 55%, 75%, 85%, 95%, 98%, or 99% enantiomeric excess of the following stereoisomers:

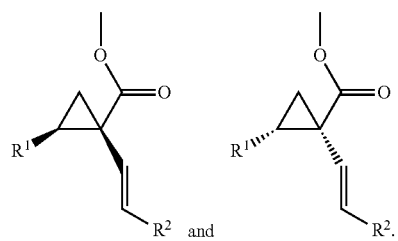

In certain embodiments, the diazo compound has the following formula,

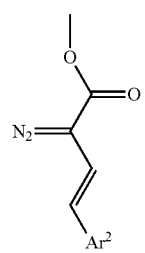

the double bond compound has the following formula,

and the synthetic compound has the following formula,

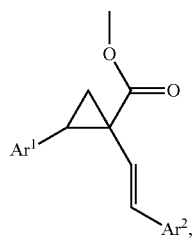

wherein $Ar^1$ and $Ar^2$ are each, the same or different, aryl optionally substituted with one or more substituents.

In certain embodiments, the synthetic product is in a composition with greater than 55%, 75%, 85%, 95%, 98%, or 99% enantiomeric excess of the following stereoisomers:

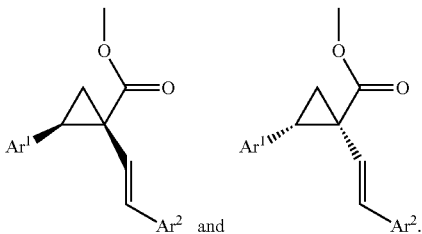

In certain embodiments, the disclosure contemplates the use of dirhodium catalysts disclosed herein in [4+3] cycloaddition reactions, e.g., mixing a diene and a vinyldiazoacetate and a dirhodium catalyst disclosed herein under conditions such that a cyclic compound is formed. See Davies et al, J. Am. Chem. Soc. 1998, 120, 3326-3331 and Reddy & Davies, J. Am. Chem. Soc., 2007, 129 (34), 10312-10313.

In certain embodiments, the diazo compound is a vinyldiazoacetate of the following formula,

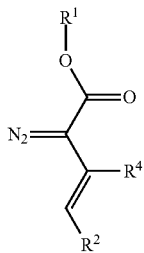

the diene compound has the following formula,

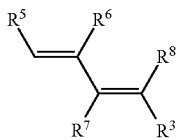

and the synthetic compound has the following formula,

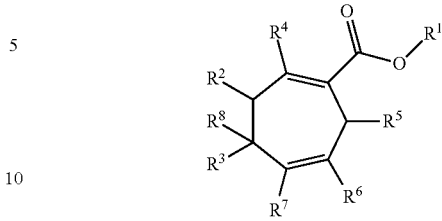

wherein, $R^1$ is alkyl, carbocyclyl, aryl, or heterocyclyl, wherein $R^1$ is optionally substituted with one or more, the same or different, $R^9$;

$R^2$ is hydrogen, alkyl, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^9$;

$R^3$ is hydrogen, alkyl, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^9$;

$R^4$ is hydrogen, alkyl, halogen, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^9$;

$R^5$ is hydrogen, alkyl, halogen, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^9$;

$R^6$ is hydrogen, alkyl, halogen, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^9$;

$R^7$ is hydrogen, alkyl, halogen, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^7$ is optionally substituted with one or more, the same or different, $R^9$;

$R^8$ is hydrogen, alkyl, halogen, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^9$;

$R^9$ is alkyl, halogen, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{10}$; and $R^{10}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the synthetic product is in a composition with greater than 55%, 75%, 85%, 95%, 98%, or 99% enantiomeric excess of the following stereoisomers:

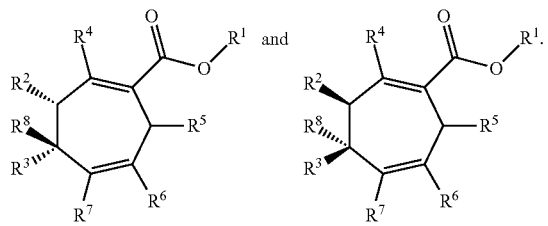

In certain embodiments, $R^1$ is alkyl optionally substituted with one or more, the same or different, $R^9$.

In certain embodiments, $R^2$ is an electron donating group selected from cyano, alkenyl, alkynyl, formyl, carbamoyl, carboxy, alkylsulfinyl, alkylsulfonyl, or arylsulfonyl, aryl, or an aromatic heterocyclyl optionally substituted with one or more, the same or different, $R^9$.

In certain embodiments; $R^2$ is aryl or an aromatic heterocyclyl optionally substituted with one or more, the same or different, $R^9$.

In certain embodiments, $R^3$ is an electron donating group selected from cyano, alkenyl, alkynyl, formyl, carbamoyl, carboxy, alkylsulfinyl, alkylsulfonyl, or arylsulfonyl, aryl, or an aromatic heterocyclyl optionally substituted with one or more, the same or different, $R^9$.

In certain embodiments, $R^3$ is aryl or an aromatic heterocyclyl optionally substituted with one or more, the same or different, $R^9$.

In certain embodiments, $R^4$ is hydrogen.

In certain embodiments, $R^5$ is hydrogen.

In certain embodiments, $R^6$ is hydrogen.

In certain embodiments, $R^7$ is hydrogen.

In certain embodiments, $R^8$ is hydrogen.

In certain embodiments, the diazo compound is a vinyldiazoacetate of the following formula,

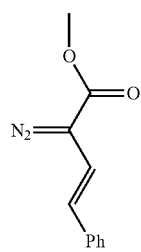

the diene compound has the following formula,

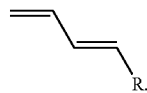

and the synthetic compound has the following formula,

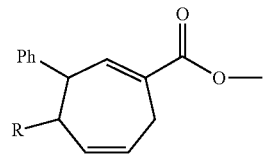

Wherein R is phenyl optionally substituted with one or more substituent.

In certain embodiments, the synthetic product is in a composition with greater than 55%, 75%, 85%, 95%, 98%, or 99% enantiomeric excess of the following stereoisomers:

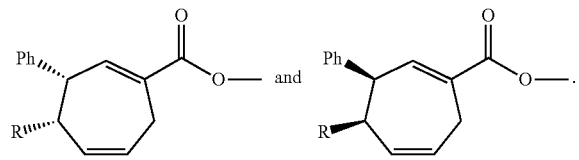

In certain embodiments, the diazo compound has the following formula,

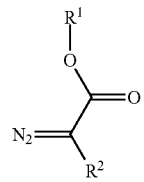

the double bond compound has the following formula,

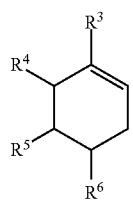

and the synthetic compound has the following formula,

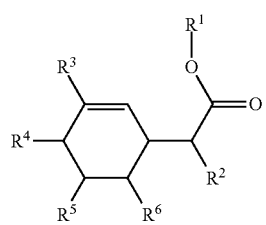

wherein, R¹ is alkyl, carbocyclyl, aryl, or heterocyclyl, wherein R¹ is optionally substituted with one or more, the same or different, R⁷;

R² is alkyl, cyano, hydroxy, amino, mercapto, formyl, carboxy, carbamoyl, alkoxy, alkanoyl, alkylthio, alkylamino, (alkyl)₂amino, alkylsulfinyl, alkylsulfonyl, arylsulfonyl, carbocyclyl, aryl, or heterocyclyl, wherein R² is optionally substituted with one or more, the same or different, R⁷;

R³ is hydrogen, alkyl, cyano, hydroxy, amino, mercapto, formyl, carboxy, carbamoyl, alkoxy, alkanoyl, alkylthio, alkylamino, (alkyl)₂amino, alkylsulfinyl, alkylsulfonyl, arylsulfonyl, carbocyclyl, aryl, or heterocyclyl, wherein R³ is optionally substituted with one or more, the same or different, R⁷;

R⁴ is hydrogen, alkyl, cyano, hydroxy, amino, mercapto, formyl, carboxy, carbamoyl, alkoxy, alkanoyl, alkylthio, alkylamino, (alkyl)₂amino, alkylsulfinyl, alkylsulfonyl, arylsulfonyl, carbocyclyl, aryl, or heterocyclyl, wherein R⁴ is optionally substituted with one or more, the same or different, R⁷;

R⁵ is hydrogen, alkyl, cyano, hydroxy, amino, mercapto, formyl, carboxy, carbamoyl, alkoxy, alkanoyl, alkylthio, alkylamino, (alkyl)₂amino, alkylsulfinyl, alkylsulfonyl, arylsulfonyl, carbocyclyl, aryl, or heterocyclyl, wherein R⁵ is optionally substituted with one or more, the same or different, R⁷; or R⁴ and R⁵ form a ring selected from a carbocyclyl, aryl, or heterocyclyl wherein the ring is optionally substituted with one or more, the same or different, R⁷

R⁶ is hydrogen, alkyl, cyano, hydroxy, amino, mercapto, formyl, carboxy, carbamoyl, alkoxy, alkanoyl, alkylthio, alkylamino, (alkyl)₂amino, alkylsulfinyl, alkylsulfonyl, arylsulfonyl, carbocyclyl, aryl, or heterocyclyl, wherein R⁶ is optionally substituted with one or more, the same or different, R⁷;

R⁷ is alkyl, halogen, cyano, hydroxy, amino, mercapto, formyl, carboxy, carbamoyl, alkoxy, alkanoyl, alkylthio, alkylamino, (alkyl)₂amino, alkylsulfinyl, alkylsulfonyl, arylsulfonyl, carbocyclyl, aryl, or heterocyclyl, wherein R⁷ is optionally substituted with one or more, the same or different, R⁸;

R⁸ is alkyl, halogen, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R⁸ is optionally substituted with one or more, the same or different, R⁹; and R⁹ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, R¹ is alkyl optionally substituted with one or more, the same or different, R⁷.

In certain embodiments, R² is an electron donating group selected from cyano, alkenyl, alkynyl, formyl, carbamoyl, carboxy, alkylsulfinyl, alkylsulfonyl, or arylsulfonyl, aryl, or an aromatic heterocyclyl optionally substituted with one or more, the same or different, R⁷.

In certain embodiments, R² is aryl or an aromatic heterocyclyl optionally substituted with one or more, the same or different, R⁷.

In certain embodiments, R³ is an electron donating group selected from cyano, alkenyl, alkynyl, formyl, carbamoyl, carboxy, alkylsulfinyl, alkylsulfonyl, or arylsulfonyl, aryl, or an aromatic heterocyclyl optionally substituted with one or more, the same or different, R⁷.

In certain embodiments, R³ is hydrogen or alkyl optionally substituted with one or more, the same or different, R⁷.

In certain embodiments, the disclosure relates to diazo compound of the following formula:

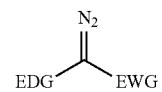

wherein EDG is an electron withdrawing group and EWG is an electron donating group. Such a diazo compound may react with a compound with a C—H bond or a N—H bond as further exemplified below. See Davies & Morton, Chem. Soc. Rev., 2011, 40, 1857-1869, hereby incorporated by reference.

In certain embodiments, the method comprises mixing the diazo compound with a compound of the following formula:

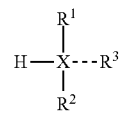

under conditions such that a synthetic compound of the following formula is formed,

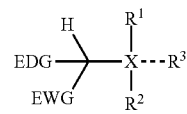

wherein X is carbon or nitrogen, wherein R³ is absent if X is nitrogen,

R¹ is alkyl, cyano, hydroxy, amino, mercapto, formyl, carboxy, carbamoyl, alkoxy, alkanoyl, alkylthio, alkylamino, (alkyl)₂amino, alkylsulfinyl, alkylsulfonyl, arylsulfonyl, carbocyclyl, aryl, or heterocyclyl, wherein R¹ is optionally substituted with one or more, the same or different, R⁴;

R² is alkyl, cyano, hydroxy, amino, mercapto, formyl, carboxy, carbamoyl, alkoxy, alkanoyl, alkylthio, alkylamino, (alkyl)₂amino, alkylsulfinyl, alkylsulfonyl, arylsulfonyl, carbocyclyl, aryl, or heterocyclyl, wherein R² is optionally substituted with one or more, the same or different, R⁴;

or R¹ and R² form a carbocyclyl, aryl, or heterocyclyl ring optionally substituted with one or more, the same or different, R⁴; or when X is carbon R¹, R², and R³ form a multicyclic carbocyclyl;

R³ is hydrogen, alkyl, cyano, hydroxy, amino, mercapto, formyl, carboxy, carbamoyl, alkoxy, alkanoyl, alkylthio, alkylamino, (alkyl)₂amino, alkylsulfinyl, alkylsulfonyl, arylsulfonyl, carbocyclyl, aryl, or heterocyclyl, wherein R³ is optionally substituted with one or more, the same or different, R⁴;

R⁴ is alkyl, halogen, cyano, hydroxy, amino, mercapto, formyl, carboxy, carbamoyl, alkoxy, alkanoyl, alkylthio, alkylamino, (alkyl)₂amino, alkylsulfinyl, alkylsulfonyl, arylsulfonyl, carbocyclyl, aryl, or heterocyclyl, wherein R⁴ is optionally substituted with one or more, the same or different, R⁵;

$R^5$ is alkyl, halogen, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$; and $R^6$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure contemplates the use of dirhodium catalysts disclosed herein for the intramolecular insertion reactions for the formation of carbon to carbon bonds. In certain embodiment, disclosure contemplates a method of making an ring structure comprising mixing a dirhodium catalyst disclosed herein and a compound comprising a diazo group and the same compound comprising a C—H bond configure about the molecule to form a five or six membered ring.

In certain embodiments, the disclosure contemplates the use of dirhodium catalysts disclosed herein in C—H aminations. In certain embodiments, the disclosure contemplates the use of dirhodium catalysts disclosed herein for the insertion reactions for the formation of carbon to nitrogen bonds, e.g., inter and intra-molecular C—H aminations. See Reddy & Davies, Org. Lett., 2006, 8, 5013-5016, hereby incorporated by reference.

In certain embodiments, the disclosure relates to a method of making an synthetic compound comprising mixing a compound with an aromatic compound, PhI(OAc)$_2$, NsNH$_2$ (4-nitrobenzenesulfonamide, and a dirhodium catalysts disclosed herein under conditions such that a synthetic compound with a C—N bond is formed.

In certain embodiments, the aromatic compound is a has the following formula

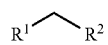

and the synthetic compound is

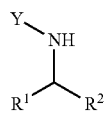

wherein, Y is 4-nitrobenzenesulfonamide or 2-nitrobenzenesulfonamide;

$R^1$ is aryl or aromatic heterocyclyl wherein $R^1$ is optionally substituted with one or more, the same or different, $R^3$;

$R^2$ is hydrogen alkyl, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^3$;

or $R^1$ and $R^2$ together with the attached atoms form a carbocyclyl, aryl, or heterocyclyl optionally substituted with one or more, the same or different, $R^3$;

$R^3$ is hydrogen, alkyl, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^4$;

$R^4$ is hydrogen, alkyl, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$;

$R^5$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the synthetic product is in a composition with greater than 55%, 75%, 85%, 95%, 98%, or 99% enantiomeric excess of the following stereioisomers:

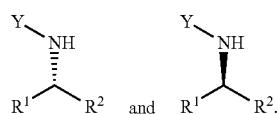

In certain embodiments, the disclosure relates to a method of making Rasagiline comprising the step of mixing 2,3-dihydro-1H-indene, PhI(OAc)$_2$, YNH$_2$, MgO, and a dirhodium catalyst disclosed herein, wherein Y is 4-nitrobenzenesulfonamide or 2-nitrobenzenesulfonamide, under conditions such that a compound of the following formula is formed,

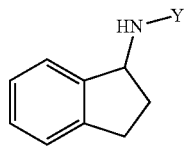

Reaction of this product with propargyl bromide in potassium carbonate provides the N substituted propargyl product. Removal of the nitrobenzenesulfonamide with DBU and HSCH$_2$CH$_2$OH provides Rasagiline. See Reddy & Davies, Org. Lett., 2006, 8, 5013-5016, hereby incorporated by reference.

EXPERIMENTAL

The following is intended to provide examples on methods of making and using embodiments of the disclosure. It is not intended to limit the scope.

$D_2$-Symmetric Dirhodium Catalyst Derived from a 1,2,2-Triarylcyclopropanecarboxylate Ligand Donor/acceptor carbenoids are also capable of generating highly substituted cyclopropanes with enantioselectivity. Cyclopropane carboxylic acids are useful ligands for dirhodium catalysts. The cyclopropane ring limits the possible conformations of the ligands and in this way addresses certain limitations observed with the $Rh_2(S\text{-}DOSP)_4$ catalyst. See FIG. 1.

To evaluate the utility of cyclopropanecarboxylate catalysts, the 1,2-diphenylcyclopropane carboxylate complex 8, $Rh_2(R\text{-}DPCP)_4$, was prepared.

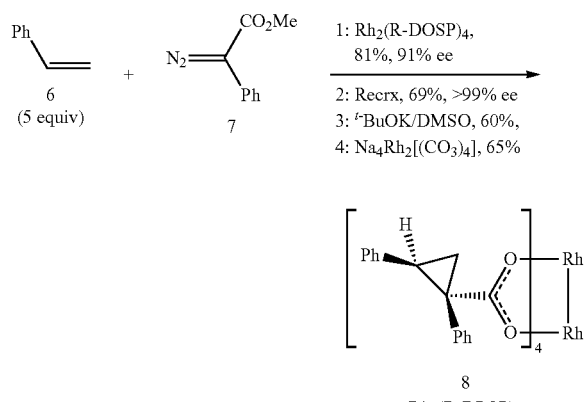

The selectivity of $Rh_2(R\text{-}DPCP)_4$ was evaluated in the standard cyclopropanation reaction between styrene 6 and styryldiazoacetate 9 using dichloromethane as solvent. The styrylcyclopropane 10 was formed in 81% yield and with high diastereoselectivity (>20:1 dr). The asymmetric induction exhibited by $Rh_2(R\text{-}DPCP)_4$ was 11% ee.

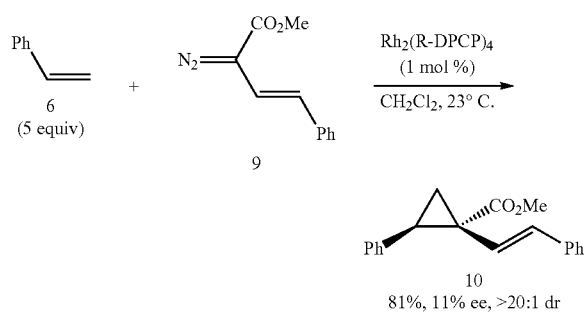

Experiments to identify a more effective cyclopropanecarboxylate ligand were instituted. Even though the cyclopropanecarboxylate in 8 has two stereogenic centers, the two phenyl rings are on the opposite side of the ring to the carboxylate. A ligand with an additional phenyl ring syn- to the carboxylate was made. The triarylcyclopropanecarboxylate, was prepared from $Rh_2(R\text{-}DOSP)_4$ catalyzed cyclopropanation reactions between 1,1-diphenylethylene (11) and para-bromophenyl diazoacetate 12.

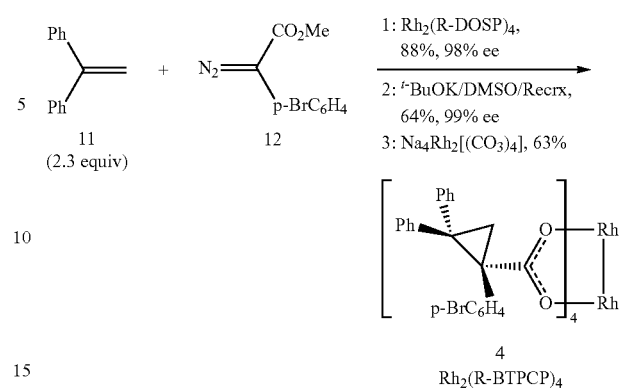

Cyclopropanation proceeds with enantioselectivity. The cyclopropane ester was converted to the corresponding carboxylic acid by tBuOK in dimethyl sulfoxide without erosion of enantioselectivity and was enriched to 99% ee after recrystallization. Standard ligand exchange conditions generated $Rh_2(R\text{-}BTPCP)_4$ (4) in 63% yield as a green solid. With $Rh_2(R\text{-}BTPCP)_4$ in hand, its efficiency was examined in the standard reaction between the styryldiazoacetate 9 and styrene 6.

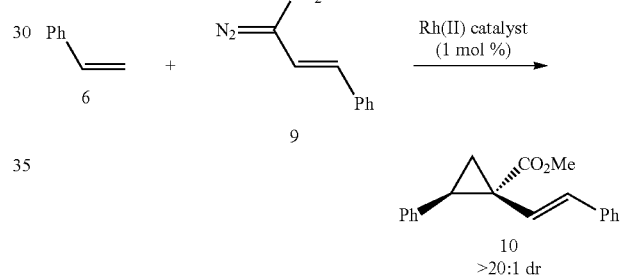

TABLE 1

Initial Evaluation of $Rh_2(R\text{-}BTPCP)_4$- and $Rh_2(R\text{-}DOSP)_4$-Catalyzed Cyclopropanation[a]

| | | | | $Rh_2(R\text{-}BTPCP)_4$ | | $Rh_2(R\text{-}DOSP)_4$ | |
|---|---|---|---|---|---|---|---|
| entry | solvent | temp. (°C) | time (h) | yield (%) | ee (%) | yield (%) | ee (%) |
| 1 | pentane | 23 | 1.5 | 82 | 84[b] | 85 | 92 |
| 2 | $CH_2Cl_2$ | 23 | 1.5 | 86 | 91 | 80 | 81 |
| 3 | $CH_2Cl_2$ | 0 | 2.0 | 72 | 92[c] | 81 | 84 |
| 4 | $CH_2Cl_2$ | −78 | 12 | 71 | 91 | 78 | 87 |
| 5[d] | $CH_2Cl_2$ | 23 | 24 | 77 | 92 | 69 | 81 |
| 6[e] | $CH_2Cl_2$ | 23 | 60 | 46 | 92 | 38 | 81 | a- Standard conditions: 9 (0.4 mmol) was added to a solution of Rh(II) catalyst and styrene (2.0 mmol) under argon over 1 h. Reported yields were obtained after chromatographic purification. dr was determined by 1H NMR prior to chromatography, and ee was determined by chiral HPLC. Absolute configuration of 10 was assigned according to previous studies.
[b] 89% ee was obtained when $Rh_2(S\text{-}BTPCP)_4$ was used.
[c] $Rh_2(S\text{-}BTPCP)_4$ was used.
[d] 0.1 mol % catalyst.
[e] 0.01 mol % catalyst.

The influence of the syn-phenyl group in the ligand was dramatic as the reaction in dichloromethane at 23° C. generated the cyclopropane 10 in 91% ee, which is better than the same reaction catalyzed by $Rh_2(R\text{-}DOSP)_4$ (81% ee), (Table 1, entry 2). Further experiments comparing $Rh_2(R\text{-}BTPCP)_4$ and Rh$_2$(R-DOSP)$_4$ are summarized in Table 1. Temperature did not influence the enantioselectivity of the Rh$_2$(R-BTPCP)$_4$-catalyzed reaction between 9 and styrene 6 as 10 was produced in 91% ee over a reaction temperature range from 23 to −78° C. (Table 1, entries 2, 4). Furthermore, decreasing the catalyst loading from 1 to 0.01 mol % did not alter the enantioselectivity (Table 1, entries 5, 6), but the reaction did not go to completion at the 0.01 mol % catalyst loading.

High asymmetric induction with Rh$_2$(S-DOSP)$_4$ is obtained when the electron-withdrawing group is a methyl ester. Changing the methyl ester to a tert-butyl ester caused a drop in the enantioselectivity. Therefore, a study was undertaken to determine how Rh$_2$(R-BTPCP)$_4$-catalyzed reactions responded to the size of the ester. See Table 2.

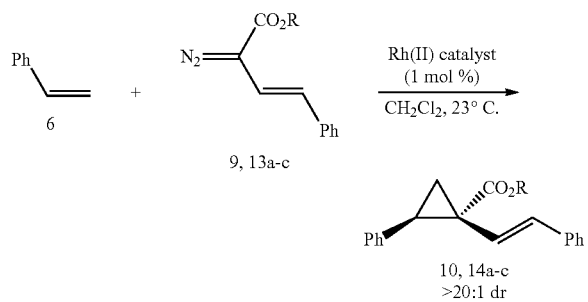

TABLE 2

Effect of Ester Size on Asymmetric Cyclopropanation

| entry | starting material | R | catalyst | product | yield (%) | ee (%) |
|---|---|---|---|---|---|---|
| 1 | 9 | Me | Rh$_2$(R-BTPCP)$_4$ | 10 | 86 | 91 |
| 2 | 13a | Et | Rh$_2$(R-BTPCP)$_4$ | 14a | 88 | 93 |
| 3 | 13b | $i$-Pr | Rh$_2$(R-BTPCP)$_4$ | 14b | 89 | 96 |
| 4 | 13c | $t$-Bu | Rh$_2$(R-BTPCP)$_4$ | 14c | 87 | 95 |
| 5 | 9 | Me | Rh$_2$(R-DOSP)$_4$ | 10 | 80 | 81 |
| 6 | 13a | Et | Rh$_2$(R-DOSP)$_4$ | 14a | 84 | 75 |
| 7 | 13b | $i$-Pr | Rh$_2$(R-DOSP)$_4$ | 14b | 84 | 75 |
| 8 | 13c | $t$-Bu | Rh$_2$(R-DOSP)$_4$ | 14c | 80 | 16 | a- Standard conditions: Diazo compound (0.4 mmol) was added to a solution of Rh(II) catalyst and styrene (2.0 mmol) in dichloromethane under argon over 1 h. Reported yields were obtained after chromatographic purification. dr was determined by $^1$H NMR prior to chromatography, and ee was determined by chiral HPLC.

Rh$_2$(R-BTPCP)$_4$ exhibited good tolerance to ester size, and the enantioselectivity actually improved on increasing the ester size from methyl to tert-butyl (Table 2, entries 1-4, from 91% ee to 95% ee). In contrast, hindered esters were confirmed to have a detrimental effect on asymmetric induction with Rh$_2$(R-DOSP)$_4$, leading to a steady drop in enantioselectivity from 81% ee to 16% ee (Table 2, entries, 5-8).

To probe the generality of this catalyst in enantioselective cyclopropanation with donor/acceptor carbenoid intermediates, various combinations of aryl- or vinyldiazoacetates with terminal alkenes were evaluated. The results for representative vinyldiazoacetates and terminal alkenes are summarized in Table 3.

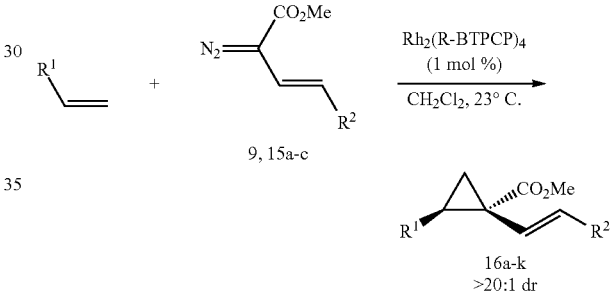

TABLE 3

Rh$_2$(R-BTPCP)$_4$-Catalyzed Asymmetric Cyclopropanation with Styryldiazoacetates

| entry | R$^1$ | diazo compound | R$^2$ | product | yield (%) | ee (%) |
|---|---|---|---|---|---|---|
| 1 | p-CF$_3$C$_6$H$_4$ | 9 | Ph | 16$^a$ | 87 | 97 |
| 2 | p-NO$_2$C$_6$H$_4$ | 9 | Ph | 16$^b$ | 92 | 95 |
| 3 | p-ClC$_6$H$_4$ | 9 | Ph | 16$^c$ | 86 | 95 |
| 4 | 3,4-diClC$_6$H$_3$ | 9 | Ph | 16$^d$ | 88 | 93 |
| 5 | p-MeOC$_6$H$_4$ | 9 | Ph | 16$^e$ | 94 | 84(93)$^b$ |
| 6 | o-CH$_3$C$_6$H$_4$ | 9 | Ph | 16$^f$ | 88 | 93 |
| 7 | o-MeO$_2$CC$_6$H$_4$ | 9 | Ph | 16$^g$ | 59 | 89 |
| 8 | H$_3$C(CH$_2$)$_3$ | 9 | Ph | 16$^h$ | 60 | 90$^c$ |
| 9 | Ph | 15$^a$ | p-ClC$_6$H$_4$ | 16$^i$ | 82 | 90 |
| 10 | Ph | 15$^c$ | 3,4-diClC$_6$H$_3$ | 16$^j$ | 79 | 86 |
| 11 | Ph | 15$^d$ | 3,4-diMeOC$_6$H$_3$ | 16$^k$ | 70 | −93$^d$ |

$^a$Standard conditions: Diazo compound (0.4 mmol) was added to a solution of Rh(II) catalyst and styrene (2.0 mmol) in dichloromethane under argon over 1 h. Reported yields were obtained after chromatographic purification. dr was determined by $^1$H NMR prior to chromatography, and ee was determined by chiral HPLC.
$^b$Reaction was conducted at −40° C.
$^c$dr > 10:1.
$^d$Rh$_2$(S-BTPCP)$_4$ was used as catalyst.

The reactions proceeded smoothly in dichloromethane, affording the corresponding cyclopropanes 16a-k with high diastereo- and enantioselectivity with yields ranging from 59% to 94%. Carbenoid precursors with electron-donating substituents on the donor group (Table 3, entry 11) resulted in higher asymmetric induction than those having electron-withdrawing substituents on the donor group (Table 3, entries 9, 10). Electron-deficient alkenes gave better enantioselectivity than electron-rich alkenes. An optimum system was identified as para-trifluoromethylstyrene and its reaction with styryldiazoacetate 9 which produced the cyclopropane 16a in 97% ee (Table 3, entry 1). In contrast, the reaction with para-methoxystyrene produced the corresponding cyclopropane 16e in 83% ee at room temperature, but this could be improved to 93% ee when the reaction was conducted at −40° C. (Table 3, entry 5). Inclusion of an ortho substituent on the styrene had little influence on the enantioselectivity, as reaction of ortho-methylstyrene and methyl 2-vinylbenzoate with the styryldiazoacetate 9 provided the cyclopropanes 16f and 16g in 93% ee and 89% ee, respectively (Table 3, entries 6, 7). Unactivated alkenes are also suitable substrates as 1-hexene (Table 3, entry 8) gave the cyclopropane 16h in 60% yield and 90% ee.

The cyclopropanation reactions of representative aryldiazoacetates are summarized in Table 4.

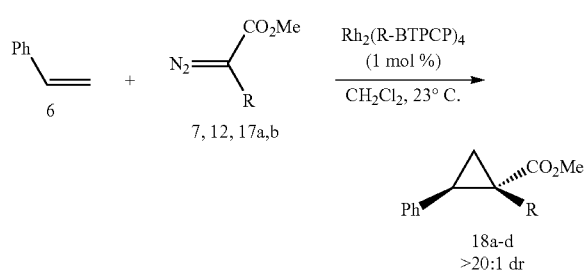

7, 12, 17a,b 18a-d
>20:1 dr

TABLE 4

Rh$_2$(R-BTPCP)$_4$-Catalyzed Asymmetric Cyclopropanation with Aryldiazoacetates

| entry | starting material | R | product | yield (%) | ee (%) |
|---|---|---|---|---|---|
| 1 | 7 | Ph | 18[a] | 82 | 83 |
| 2 | 12 | p-BrC$_6$H$_4$ | 18[b] | 80 | 85 |
| 3 | 17[a] | p-MeOC$_6$H$_4$ | 18[c] | 74 | 91 |
| 4 | 17[b] | p-CF$_3$C$_6$H$_4$ | 18[d] | 86 | 89 |

[a]Standard conditions: Diazo compound (0.4 mmol) was added to a solution of Rh(II) catalyst and styrene (2.0 mmol) in dichloromethane under argon over 1 h. Reported yields were obtained after chromatographic purification. dr was determined by $^1$H NMR prior to chromatography, and ee was determined by chiral HPLC.
[b]Reaction was conducted at −40° C.
[c]dr > 10:1.
[d]Rh$_2$(S-BTPCP)$_4$ was used as catalyst.

The reactions generated the cyclopropanes 18a-d in high yield and stereoselectivity (>20:1 dr, 83-91% ee), with p-methoxyphenyl derivative 17a giving the highest enantioselectivity (91% ee). These results are similar to the reported results for the Rh$_2$(S-DOSP)$_4$-catalyzed cyclopropanations of aryldiazoacetates in hexane as solvent.

Encouraged by the cyclopropanation results, it was decided to investigate the scope of the catalyst further by looking at more elaborate reactions of vinyldiazoacetates. When vinyldiazoacetates react with dienes, a formal [4+3] cycloaddition occurs by a tandem cyclopropanation/Cope rearrangement. See Table 5.

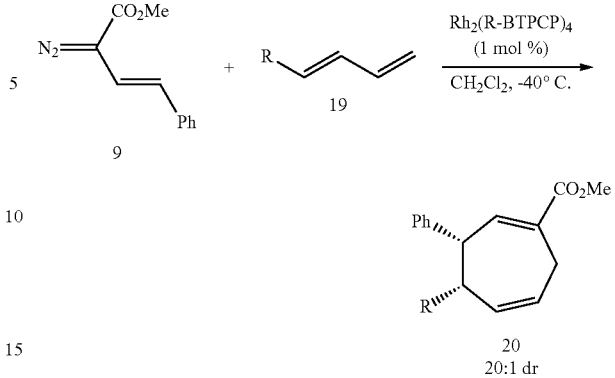

20
20:1 dr

TABLE 5

Rh$_2$(R-BTPCP)$_4$ Catalyzed Tandem Cyclopropanation/Cope Rearrangement

| entry | starting diene | R | product | yield (%) | ee (%) |
|---|---|---|---|---|---|
| 1 | 19[a] | Ph | 20[a] | 56 | 87 |
| 2 | 19[b] | p-CF$_3$C$_6$H$_4$ | 20[b] | 71 | 91 |
| 3 | 19[c] | p-MeOC$_6$H$_4$ | 20[c] | 60 | 89 |

[a]Standard conditions: Diazo compound (0.4 mmol) was added to a solution of Rh(II) catalyst and styrene (2.0 mmol) in dichloromethane at −40° C. under argon over 1 h. Reported yields were obtained after chromatographic purification. dr was determined by $^1$H NMR prior to chromatography, and ee was determined by chiral HPLC. Absolute configuration of the products was assigned according to previous studies.

The Rh$_2$(R-BTPCP)$_4$-catalyzed reactions of styryldiazoacetate 9 with dienes 19 gave rise to the cycloheptadienes 20 in 56-71% yield and the enantioselectivity was 87-91% ee. Compounds 20 were formed as single diastereomers.

Vinyldiazoacetates are useful in a range of C—H functionalization reactions. An example is the formal C—H functionalization of dihydronaphthalene 21 to form 22.

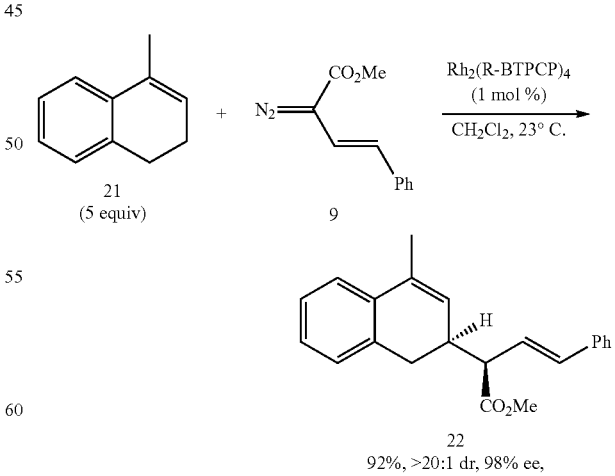

Figure 9:
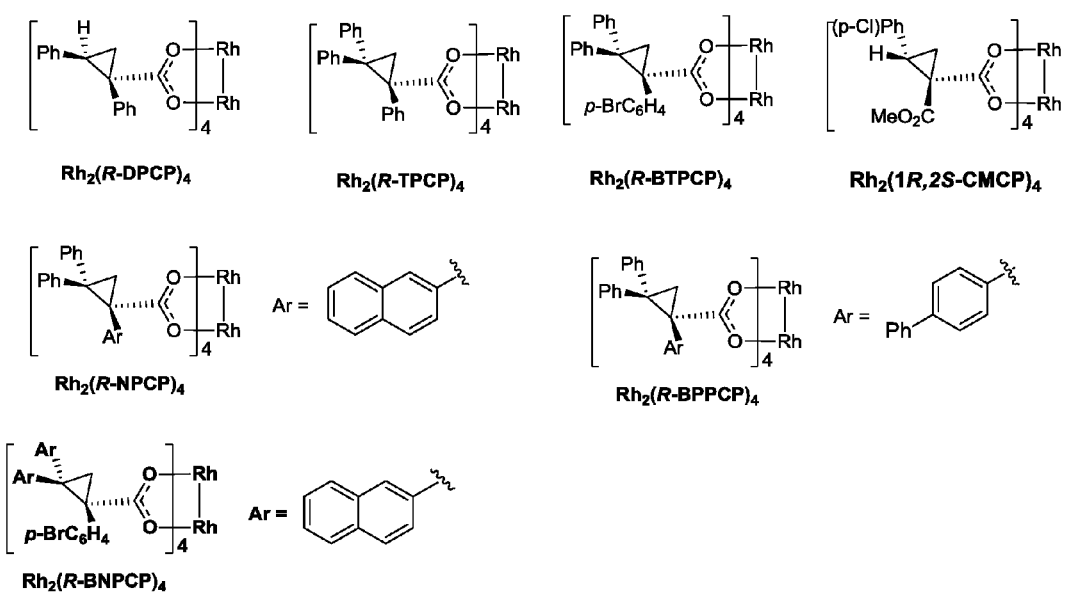
FIG. 9 illustrates additional embodiments of the disclosure.

22
92%, >20:1 dr, 98% ee,

Catalysts with cyclopropane rings containing three aromatic rings as gave asymmetric induction, see Table 6 and FIG. 9.

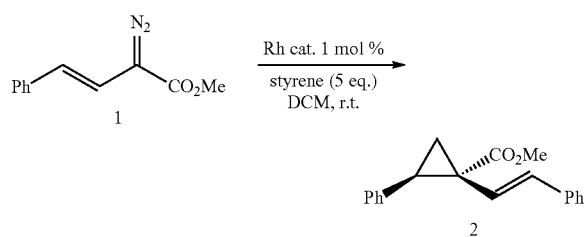

TABLE 6

Dirhodium Catalysts with Different Substituents

| entry | catalyst | yield (%) | ee (%) |
|---|---|---|---|
| 1 | $Rh_2(R\text{-}DPCP)_4$ | 81 | 11 |
| 2 | $Rh_2(R\text{-}TPCP)_4$ | 84 | 79 |
| 3 | $Rh_2(R\text{-}BTPCP)_4$ | 86 | 91 |
| 4 | $Rh_2(1R,2S\text{-}CMCP)_4$ | 81 | 22 |
| 5 | $Rh_2(R\text{-}NPCP)_4$ | 77 | 94 |
| 6 | $Rh_2(R\text{-}BPPCP)_4$ | 76 | 84 |
| 7 | $Rh_2(S\text{-}BNPCP)_4$ | 74 | −87 |

Although it is not intended that certain embodiments, of the disclosure be limited by any particular mechanism, it is believed that this reaction proceeds by a sequence involving a combined C—H functionalization/Cope rearrangement followed by a reverse Cope rearrangement. When this reaction was catalyzed by $Rh_2(R\text{-}BTPCP)_4$, the product 22 was formed in 92% yield as a single diastereomer and in 98% ee. This result compares favorably to the $Rh_2(S\text{-}DOSP)_4$-catalyzed formation of 22 with hexane as solvent.

Figure 2:
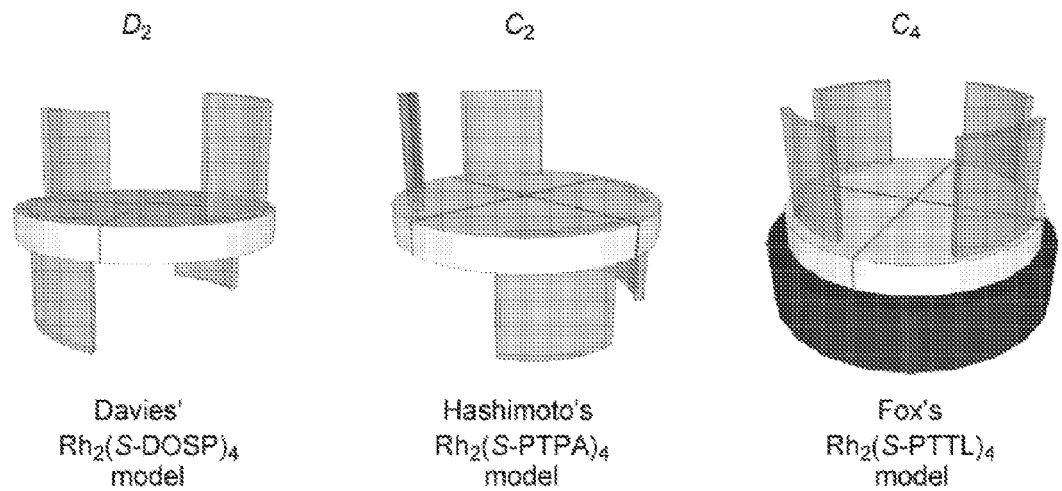
FIG. 2 illustrates three distinct ligand orientations used to rationalize enantioselectivity in dirhodium carboxylate-catalyzed reactions.

Even though dirhodium tetracarboxylates contain two potentially reactive rhodium sites and four identical ligands of C1 symmetry, they are capable of very high asymmetric induction. Although it is not intended that embodiments of this disclosure be limited by any particular mechanism, it is believed that the dirhodium tetracarboxylates are in conformations of higher symmetry than the ligands themselves. For $Rh_2(S\text{-}DOSP)_4$-catalyzed reactions, the catalyst is proposed to preferentially exist in a D2 symmetric "up-down-up-down" conformation, providing identical C2 symmetric binding sites at both rhodium faces of the catalyst (FIG. 2). Hashimoto rationalized the selectivity of his phthalimido amino acid derived catalysts by proposing a C2 symmetric "up-up-down-down" arrangement for the catalyst. More recently, Fox reported that the tert-butyl catalyst $Rh_2(S\text{-}PTTL)_4$, the most broadly used of Hashimoto's catalysts, exists in an "all-up" distorted C4 conformation. According to this model, the bulky tert-butyl groups are necessary to limit reactivity to only one of the Rh faces of the catalyst, whereas a distorted C4 symmetric chiral crown-like ligand arrangement guides the facial selectivity at the open Rh-face. Recently, other groups have reported X-ray structures of related catalysts to $Rh_2(S\text{-}PTTL)_4$, and all these catalysts adopt an "all-up" C4 conformation. Because $Rh_2(R\text{-}BTPCP)_4$ is structurally different from the other above-mentioned chiral dirhodium tetracarboxylate catalysts, a study to determine what made it such an effective chiral catalyst was undertaken.

Figure 3:
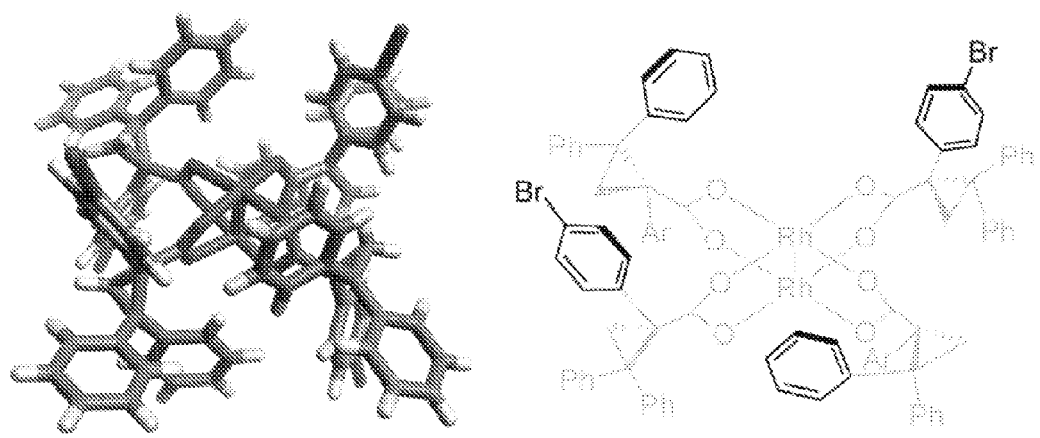
FIG. 3 illustrates $Rh_2(R\text{-}BTPCP)_4$ (axial ligands omitted for clarity) indicated by data from an X-ray crystal structure study.

A single crystal X-ray diffraction analysis of $Rh_2(R\text{-}BTPCP)_4$ provided valuable insights into the catalyst geometry. In the X-ray structure, the large chiral ligands of $Rh_2(R\text{-}BTPCP)_4$ are organized in an overall D2 symmetric arrangement, forming identical rectangular orthogonal (approximately 8.5×10.5 Å) binding cavities of C2 symmetry at the two catalytically active axial termini of the rhodium dimer (FIG. 3).

Figure 4:
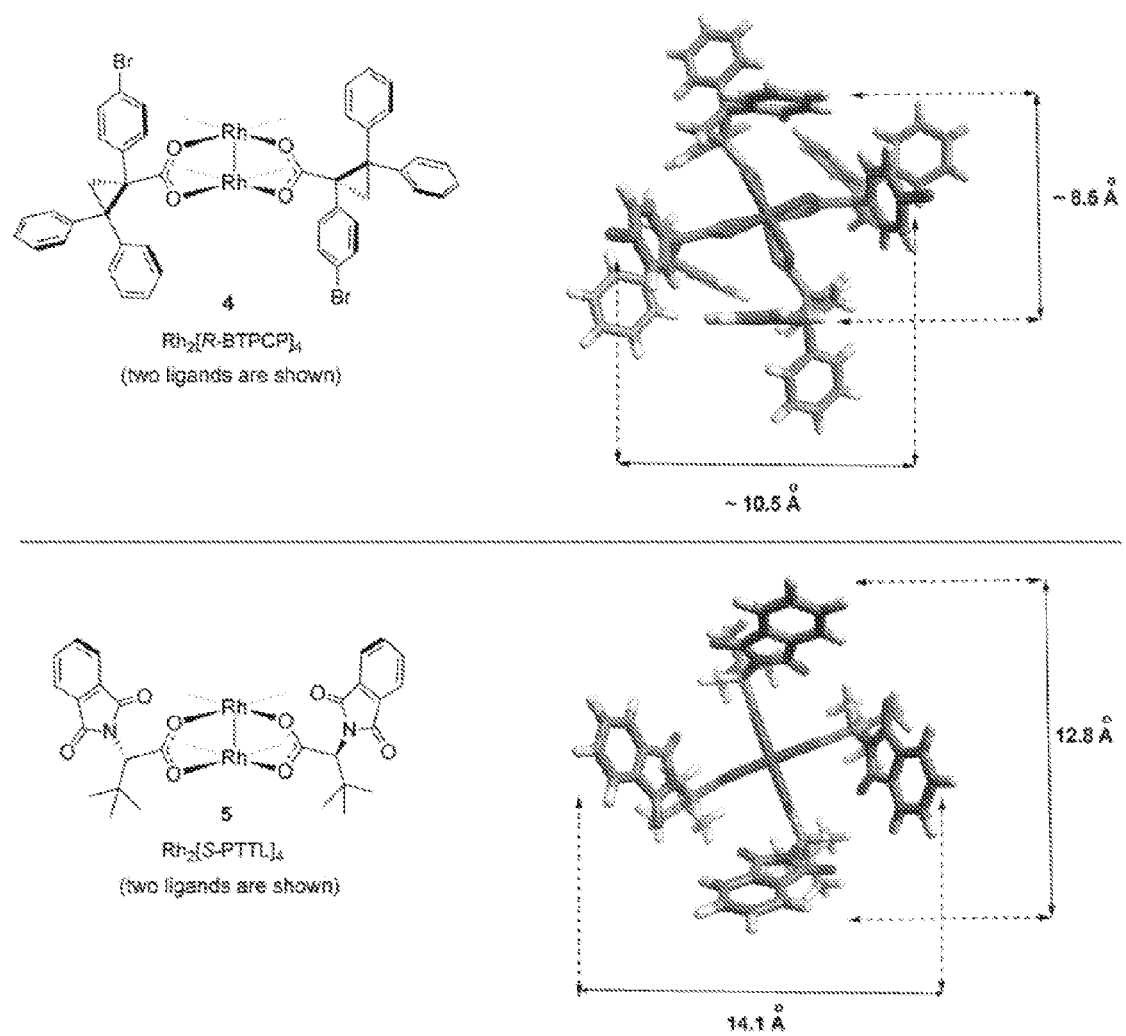
FIG. 4 illustrates the calculated structure catalytically active sites of $Rh_2(R\text{-}BTPCP)_4$ (X-ray) and $Rh_2(S\text{-}PTTL)_4$.

$Rh_2(R\text{-}BTPCP)_4$ and $Rh_2(S\text{-}PTTL)_4$ have different overall symmetry, D2 and distorted C4, respectively, but they possess a related rectangular binding cavity at the reactive axial positions (FIG. 4). The rectangular biding cavity for $Rh_2(R\text{-}BTPCP)_4$ (8.5×10.5 Å) is significantly smaller than the cavity for $Rh_2(S\text{-}PTTL)_4$ (12.8×14.1 Å). Furthermore, both Rh faces of $Rh_2(R\text{-}BTPCP)_4$ have identical binding cavities of C2 symmetry. However, for $Rh_2(S\text{-}PTTL)_4$ only one Rh face has the rectangular binding cavity, whereas the other face is considered to be blocked by the tert-butyl groups. According to the $Rh_2(S\text{-}PTTL)_4$ model proposed by Fox, a carbene would align with the wide dimension of the catalyst leaving the Si face open for the attack because of the wider gap between two of the ligands. To test if the same model could be utilized to explain the stereochemical outcome of $Rh_2(R\text{-}BTPCP)_4$-catalyzed transformations, a computational analysis of the catalyst-carbene complex was conducted.

Figure 5:
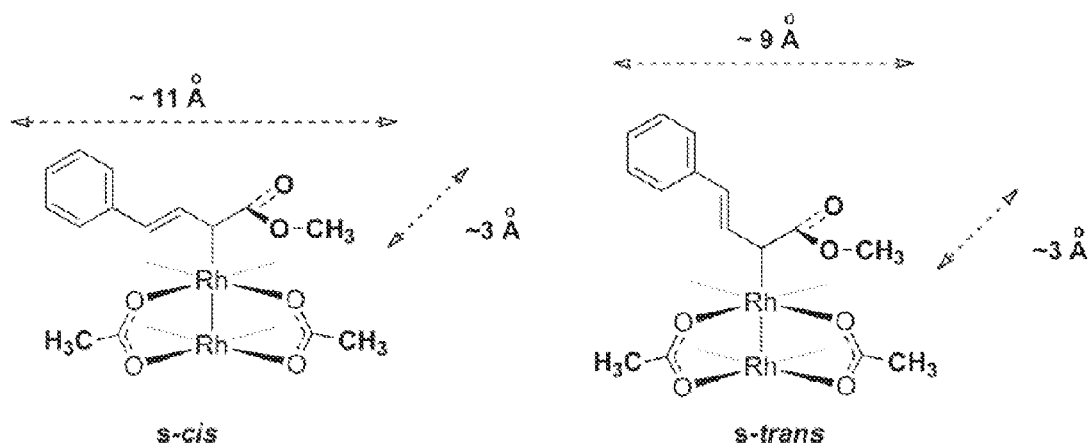
FIG. 5 illustrates data from a DFT model of s-cis and s-trans carbine conformers.

Traditional computational approaches to analyze dirhodium carbene complexes have tended to rely on the X-ray structure of the catalyst in combination with DFT optimized geometries of the carbenoid with a simplified, achiral, catalyst model. Although such analysis may provide preliminary insights into the catalyst selectivity, more precise studies accounting for interactions between the carbene and ligands, as well as ligand mobility in these systems would give a much better understanding of the role of the chiral catalyst. In fact, our preliminary DFT calculations on the simplified model of the dirhodium(tetracarboxylate)-carbene complex (FIG. 5) demonstrates the importance of such studies. A comparison of the DFT optimized geometries, given in FIG. 5, with the reported size of the catalyst binding cavity (FIG. 4) reveals that even the shortest s-trans carbenoid conformation would not fit into the tight environment (the dimensions shown on FIGS. 4 and 5 were measured from atomic centers and do not account for atomic radii) of the $Rh_2(R\text{-}BTPCP)_4$ catalyst.

Figure 6:
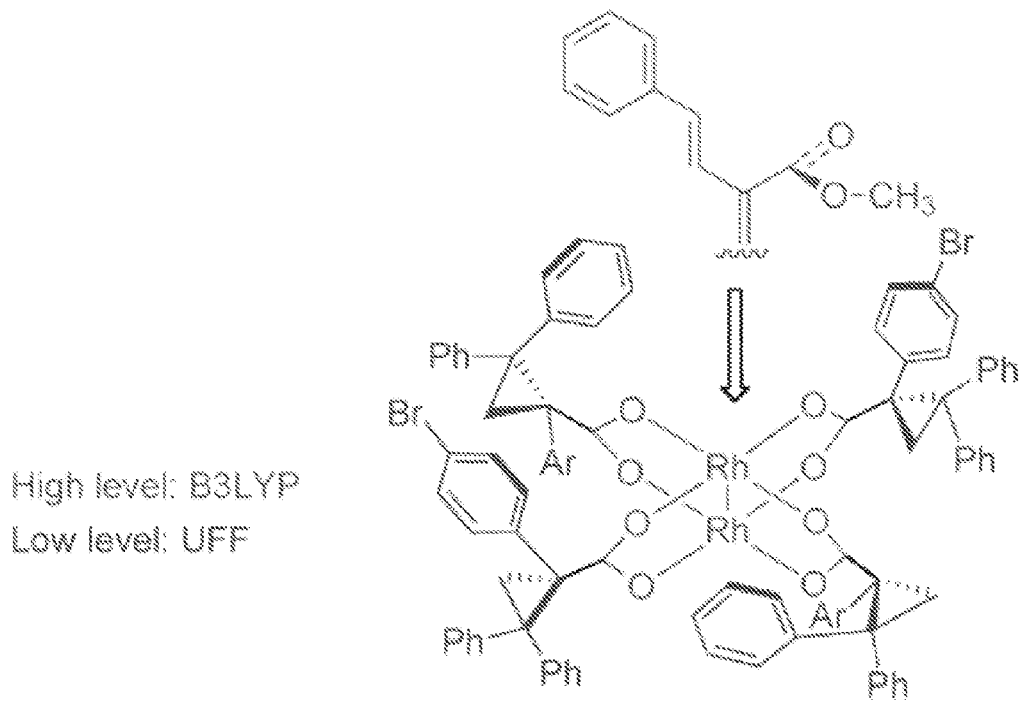
FIG. 6 illustrates ONIOM partitioning of $Rh_2(R\text{-}BTPCP)_4$-carbene complex.

Performing DFT calculations on the complete rhodium carbene complex (approximately 200 atoms) would be impractical unless very small basis sets were used, and these may not give a realistic representation of the complex. Therefore, we employ an alternative ONIOM approach to study the carbenoid reaction. A two-layer ONIOM (QM:MM) method used in these studies divides the whole system into two subsystems (denoted "model" and "real" layers). The ONIOM partitioning of the catalyst-carbene system that was used is shown in FIG. 6. In these studies the B3LYP and UFF methods were used for the calculations of the "model" (in red) and "real" (in blue) layers, respectively. Such partition provided an description for the central rhodium carboxylate-carbene complex and accounted for the steric influence of the surrounding ligands.

Figure 7:
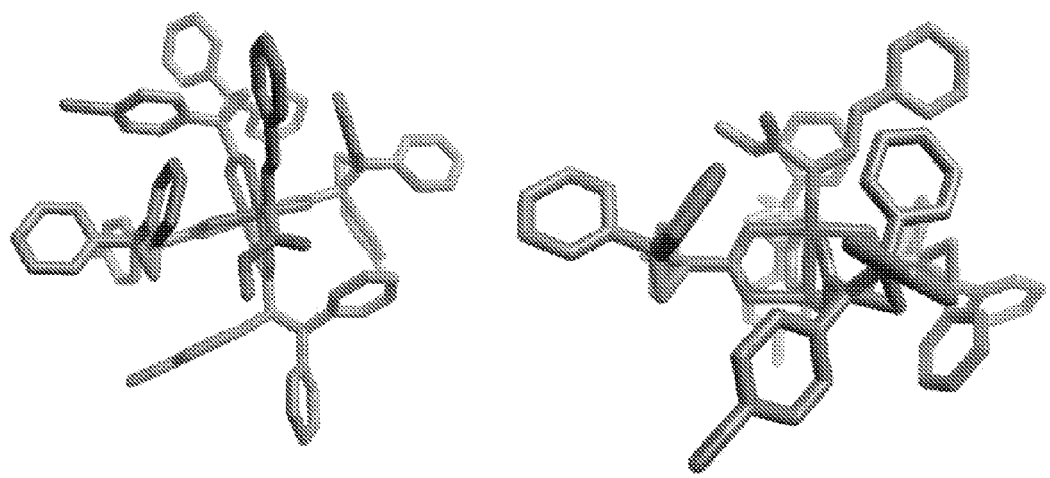
FIG. 7 illustrates the calculated lowest-energy conformation of s-trans carbine, top view (left) and side view (right). Hydrogens atoms were omitted for clarity.

Our computational results support the importance of the steric environment within the catalyst. Thus even the best matching combination of the shortest s-trans carbene aligned with the widest dimension of the orthogonal binding cavity caused steric repulsions significant enough to rotate two para-bromophenyl groups in either conrotary or disrotary directions. A similar result was obtained when the s-trans carbene was aligned with the shortest catalyst dimension; this time the phenyl groups rotated in a similar way. Sixteen distinct minima were located on the potential energy surface corresponding to different conformations of the s-trans carbene with $Rh_2(R\text{-}BTPCP)_4$. The lowest energy conformation, separated from the closest one by $\Delta E=1.8$ kcal/mol is depicted in FIG. 7. In this conformer two ligands rotated in a conrotary fashion to minimize steric interactions with the carbene, whereas the other two ligands remained in the upward position to reduce steric repulsions with the neighboring ligands. This arrangement resulted in a C2 symmetric environment at the carbene site cavity containing two phenyl rings and two para-bromophenyl groups. One of the rings is blocking the donor group (aryl, styryl) while the other one is positioned next to the acceptor group (ester). The same ligand conformation having the s-cis carbene geometry was found to be 2.5 kcal/mol higher.

Figure 8:
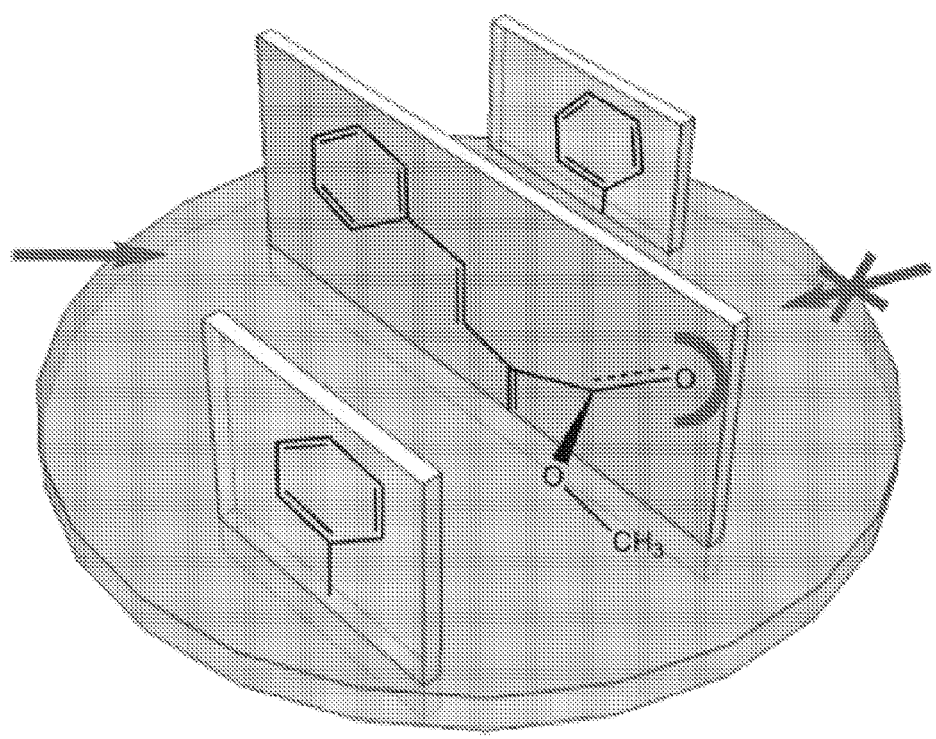
FIG. 8 illustrates a predictive stereochemical model for $Rh_2(R\text{-}BTPCP)_4$-catalyzed transformation.

Although it is not intended that embodiments of the disclosure be limited by any mechanism, a stereochemical model that explains the selectivity observed in $Rh_2(R$-$BT$-$PCP)_4$ catalyzed transformations is proposed in FIG. 8 basis on the computational data above. The substrate approaches donor/acceptor-substituted rhodium-carbenoids over the donor group. The ester group aligns perpendicular to the carbene plane, and blocks attack on its side. When the substrate approaches over the donor group, the Re-face is blocked by the aryl ring of the ligand leaving the Si-face open for the attack. This model predicts correctly the observed absolute configuration of the products.

Synthesis of Dirhodium tetrakis((1S,2R)-1,2-diphenylcyclopropanecarboxylate (8)

(1S,2R)-methyl 1,2-diphenylcyclopropanecarboxylate

To a flame-dried round bottom flask kept under a dry atmosphere of argon, was added $Rh_2(RDOSP)_4$ (0.01 equiv., 379 mg), styrene (2.32 equiv., 13.7 mL), and dry degassed pentane (100 mL) at room temperature. A solution of methyl 2-diazo-2-phenylacetate 7 (1.0 equiv., 3.52 g) in dry, degassed pentane (100 mL) was then added to the former solution drop-wise over 3 hours under argon atmosphere. The mixture was then allowed to stir for overnight, and concentrated in vacuo. The crude residue was analyzed by $^1$H NMR and purified by flash column chromatography eluting with a 50:1 mixture of hexanes/ethyl acetate to provide the product as a white solid (4.08 g, 81% yield, 91% ee). Recrystallization with a 100:1 mixture of hexane/ethyl acetate afforded the enantioenriched product (2.82 g, 69% yield, >99% ee). $^1$H NMR (400 MHz, CDCl$_3$): δ 7.17-7.15 (m, 3H), 7.09-7.05 (m, 5H), 6.81-6.79 (m, 2H), 3.69 (s, 3H), 3.15 (dd, J=9.4, 7.3 Hz, 1H), 2.18 (dd, J=9.4, 5.0 Hz, 1H), 1.92 (dd, J=7.3, 5.0 Hz, 1H); HPLC (S,S-Whelk, 1.5% isopropanol in hexane, 0.7 mL/min, 1 mg/mL, 30 min, UV 254 nm) retention times of 12.9 min (major) and 15.4 min (minor), 91% ee.

(1S,2R)-1,2-diphenylcyclopropanecarboxylic acid

To a round-bottom flask at room temperature was added (1S,2R)-methyl 1,2-diphenylcyclopropanecarboxylate (11.5 mmol, 2.91 g, 1.0 equiv.) in dry DMSO (24 mL). t-BuOK (25.4 mmol, 2.85 g, 2.2 equiv.) was added in several portions over 30 minutes under argon. The reaction was monitored by TLC technique until the starting material was consumed completely. The reaction mixture was cooled with ice bath and acidified by careful addition of saturated ammonium chloride (10 mL), followed by a slow addition of 1 N HCl aqueous (35 mL) with vigorous stirring until the pH value reached 3-4. Light yellow solid precipitate was collected by filtration, washed with water (3×5 mL), dissolved in ethyl acetate (100 mL), washed with brine (3×5 mL), dried over MgSO4, and concentrated in vacuo. The crude material was purified using flash column chromatography eluting with a 10:1 mixture of hexanes/ethyl acetate to provide the desired product as a white solid (1.64 g, 60% yield, >99% ee). $^1$H NMR (400 MHz, CDCl$_3$) δ 7.15-7.14 (m, 3H), 7.08-7.03 (m, 5H), 7.06-6.79 (m, 2H), 3.18 (dd, J=9.4, 7.4 Hz, 1H), 2.21 (dd, J=9.4, 4.9 Hz, 1H), 1.97 (dd, J=7.4, 4.9 Hz, 1H); $^{13}$C NMR (100 MHz, CDCl$_3$) δ 179.8, 136.1, 134.2, 132.1, 128.3, 127.99, 127.97, 127.5, 126.7, 37.4, 34.1, 20.9; HPLC (to improve the separation, the product was converted to the corresponding methyl ester prepared using dimethylsulfate/KOH in tetrahydrofuran under reflux), (S,S-Whelk, 1.5% isopropanol in hexane, 0.7 mL/min, 1 mg/mL, 30 min, UV 254 nm) retention times of 12.5 min (major) and 15.5 min (minor), >99% ee.

Dirhodium tetrakis((1S,2R)-1,2-diphenylcyclopropanecarboxylate (8)

A solution of sodium rhodium carbonate [Na$_4$Rh$_2$(CO$_3$)$_4$]-2.5H$_2$O (501 mg, 1.0 equiv.) and (1S,2R)-1,2-diphenylcyclopropanecarboxylic acid (1.64 g, 8.0 equiv.) in 35 mL distilled water was refluxed for 2 days under argon, and then the solution was extracted with dichloromethane (3×50 mL), organic extracts were combined, and then washed with saturated sodium bicarbonate (3×10 mL), brine (3×10 mL), dried over anhydrous MgSO$_4$, and concentrated in vacuo. The crude material was purified using flash column chromatography eluting with a 100:1 mixture of toluene and acetonitrile mixtures to provide the desired catalyst 8 as a green solid (650 mg, 65%). mp: 222-224° C.; $R_f$=0.20 (toluene/acetonitrile=20/1); [α]20 D 265.1° (c=0.02, CHCl$_3$); $^1$H NMR (400 MHz, CDCl$_3$): δ 7.10-7.05 (m, 24H), 6.94-6.92 (m, 8H), 6.74-6.72 (m, 8H), 2.96 (dd, J=9.2, 7.2 Hz, 1H), 2.04 (dd, J=9.2, 4.8 Hz, 1H), 1.77 (dd, J=7.2, 4.8 Hz, 1H); $^{13}$C NMR (100 MHz, CDCl$_3$) δ 191.6, 136.8, 135.4, 131.7, 127.9, 127.6, 127.5, 126.7, 126.1, 60.3, 39.5, 32.9, 19.7; IR (neat): 3028, 1682, 1577, 1497, 1398; HRMS (ESI) calcd for C64H52O8ClRh2 (M+Cl)$^+$ 1189.14663. found 1189.14675.

Synthesis of Dirhodium Tetrakis(1-(4-bromophenyl)-2,2-diphenylcyclopropane carboxylate (4)

(R)-methyl 1-(4-bromophenyl)-2,2-diphenylcyclopropanecarboxylate

To a flame-dried round bottom flask kept under a dry atmosphere of argon, was added Rh$_2$(RDOSP)$_4$ (0.01 equiv., 382 mg), 1,1-diphenylethlyene 11 (2.32 equiv., 8.16 mL), and dry degassed pentane (100 mL). A solution of freshly prepared methyl 2-(4-bromophenyl)-2-diazoacetate 12 (1.0 equiv., 5.1 g) in dry, degassed pentane (150 mL) was added to the former solution drop-wise over 3 hours at room temperature. The mixture was allowed to stir overnight, and then concentrated in vacuo. The crude material was purified using flash column chromatography eluting with a 50:1 mixture of hexanes/ethyl acetate to provide the desired product as a white foam (7.2 g, 88% yield, 98% ee). mp: 82-85° C.; $R_f$=0.55 (hexanes/ethyl acetate=7/1); [α]20 D −289.2° (c=1.17, CHCl$_3$); $^1$H NMR (400 MHz, CDCl$_3$) δ 7.48-7.47 (m, 2H), 7.35-7.31 (m, 2H), 7.27-7.18 (m, 5H), 7.02-6.97 (m, 5H), 3.34 (s, 3H), 2.68 (d, J=5.5 Hz, 1H), 2.39 (d, J=5.9 Hz, 1H); $^{13}$C NMR (100 MHz, CDCl$_3$) δ 170.9, 141.7, 139.1, 134.8, 133.5, 130.6, 129.8, 128.5, 128.3, 127.7, 126.9, 126.3, 121.1, 52.2, 44.6, 42.4, 22.6; IR (neat): 3057, 3024, 2947, 1724, 1490, 1217; HRMS (APCI) calcd for C23H20BrO2 (M+H)$^+$ 407.06412. found 407.06432; HPLC (S,S-Whelk, 5% isopropanol in hexane, 0.8 mL/min, 1 mg/mL, 60 min, UV 254 nm) retention times of 10.6 min (major) and 50.9 min (minor), 98% ee. (S)-methyl 1-(4-bromophenyl)-2,2-diphenylcyclopropanecarboxylate was prepared by the same procedure with Rh$_2$(S-DOSP)$_4$ as the catalyst, $[α]^{20}_D$: 219.6° (c=1.32, CHCl$_3$).

(R)-1-(4-bromophenyl)-2,2-diphenylcyclopropanecarboxylic acid

To a round-bottom flask at room temperature was added (R)-methyl 1-(4-bromophenyl)-2,2-diphenylcyclopropanecarboxylate (17.9 mmol, 7.3 g, 1.0 equiv) in dry DMSO (35 mL). t-BuOK (39.6 mmol, 4.4 g, 2.2 equiv) was added in several portions over 30 minutes under argon. The reaction was monitored by TLC technique until the starting material was consumed completely. The reaction mixture was cooled with ice bath and acidified by saturated ammonium chloride aqueous (15 mL), followed by a slow addition of 1 N HCl (50 mL) with vigorous stirring until the pH value reached 3-4. Sticky solid precipitate was collected by filtration, washed with water (3×5 mL), dissolved in ethyl acetate (150 mL), washed with brine (3×10 mL), dried over anhydrous $MgSO_4$, and concentrated in vacuo. The crude material was purified using flash column chromatography eluting with a 4:1 mixture of hexanes/ethyl acetate to provide the desired product as a white solid (4.9 g, 69% yield). Recrystallization in pentane/ethyl acetate (50/1) provided the enantioenriched product as a white solid (4.46 g, 64% yield, 99% ee). (S)-1-(4-bromophenyl)-2,2-diphenylcyclopropanecarboxylic acid was prepared by the same procedure, $[\alpha]^{20}_D$ 260.4° (c=1.37, $CHCl_3$). mp: 180-182° C.; $R_f$=0.21 (hexanes/ethyl acetate=5/1); $[\alpha]20$ D −224.8° (c=3.77, $CHCl_3$); $^1H$ NMR (400 MHz; $CDCl_3$) δ 7.44-7.42 (m, 2H), 7.29-7.22 (m, 5H), 7.13-7.11 (m, 2H), 6.99-6.93 (m, 5H), 2.56 (d, J=5.6 Hz, 1H), 2.41 (d, J=5.6 Hz, 1H); $^{13}C$ NMR (100 MHz, $CDCl_3$) δ 176.7, 141.2, 138.9, 134.3, 133.5, 130.6, 129.7, 128.5, 128.4, 127.8, 127.1, 126.5, 121.3, 45.8, 41.9, 23.1; IR (neat): 3024, 1688, 1489, 1449; HRMS (APCI) calcd for C22H16BrO2 (M−H)$^+$ 391.03391. found 391.03446; HPLC (to improve the separation, the product was converted to the corresponding methyl ester prepared using dimethylsulfate/KOH in tetrahydrofuran under reflux), (S,S-Whelk, 5% isopropanol in hexane, 0.8 mL/min, 1 mg/mL, 60 min, UV 254 nm) retention times of 10.7 min (major) and 49.8 min (minor), 99% ee.

Dirhodium tetrakis((R)-1-(4-bromophenyl)-2,2-diphenylcyclopropanecarboxylate) (4)

A solution of sodium rhodium carbonate [$Na_4Rh_2(CO_3)_4$]-2.5$H_2O$ (557 mg, 1.0 equiv.) and (R)-1-(4-bromophenyl)-2,2-diphenylcyclopropanecarboxylic acid (3.0 g, 8.0 equiv.) in 60 mL distilled water was refluxed for 3 days under argon, and then the solution was extracted with dichloromethane (3×100 mL), organic extracts were combined, washed with saturated sodium bicarbonate (3×10 mL), 10% sodium hydroxide (3×10 mL), brine (3×10 mL), dried over anhydrous $MgSO_4$, and concentrated in vacuo. The crude material was purified using flash column chromatography eluting with a 50:1 mixture of toluene and acetonitrile to provide the desired catalyst 4 as a green solid (1.07 g, 63% yield). mp: 235-237° C.; $R_f$=0.25 (toluene/acetonitrile=50/1); $[\alpha]^{20}_D$ −41.7° (c=0.02, $CHCl_3$); $^1H$ NMR (400 MHz, $CDCl_3$): δ 7.23-7.15 (m, 7H), 6.90-6.81 (m, 7H), 2.30 (d, 1H, J=5.0 Hz), 2.39 (d, 1H, J=5.0 Hz). $^{13}C$ NMR (100 MHz, $CDCl_3$) δ 188.9, 142.4, 140.8, 135.7, 132.8, 130.6, 129.9, 129.2, 128.3, 127.9, 126.6, 126.4, 120.9, 46.9, 42.7, 23.6; IR (neat): 1577, 1490, 1447, 1397, 1379, 1277, 1156, 1076, 1010, 991, 906, 823, 777, 733; HRMS (ESI) calcd for C88H64Br4O8 (M)$^+$ 1769.9444. found 1769.94392. $Rh_2(S-BTPCP)_4$ was prepared with the same procedure, $[\alpha]^{20}_D$ 140.9° (c=0.02, $CHCl_3$).

Preparation of [$Rh_2(R-NPCP)_4$]

(R)-methyl 1-(naphthalen-2-yl)-2,2-diphenylcyclopropanecarboxylate

To a flame-dried round bottom flask kept under a dry atmosphere of argon, was added $Rh_2(R-DOSP)_4$ (0.01 equiv., 474 mg), 1,1-diphenylethlyene (2.32 equiv., 10.5 g, 58 mmol), and dry degassed pentane (100 mL). A solution of freshly prepared methyl 2-diazo-2-(naphthalen-2-yl)acetate (1.0 equiv., 5.65 g, 25 mmol) in dry, degassed pentane (250 mL) was added to the former solution drop-wise over 3 hours at −40° C. The mixture was allowed to stir overnight to room temperature, and then concentrated in vacuo. The crude material was purified using flash column chromatography eluting with a 40:1 mixture of hexanes/ethyl acetate to provide the desired product as a white solid (7.0 g, 74% yield, >99% ee). mp: 138-139° C.; $[\alpha]^{20}_D$ −347.9° (c=1.0, $CHCl_3$); $^1H$ NMR (400 MHz, $CDCl_3$) δ 7.78 (s, 1H), 7.74-7.71 (m, 1H), 7.50-7.36 (m, 4H), 7.24-7.22 (m, 1H), 7.06-7.04 (m, 2H), 6.96-6.86 (m, 3H), 3.38 (s, 3H), 2.79 (d, J=5.6 Hz, 1H), 2.57 (d, J=5.6 Hz, 1H); $^{13}C$ NMR (100 MHz, $CDCl_3$) δ 171.4, 141.9, 139.4, 133.6, 132.8, 132.3, 130.4, 130.2, 129.9, 128.7, 128.3, 127.7, 127.6, 127.5, 126.9, 126.7, 126.1, 125.8, 125.6, 141.9, 139.4, 133.6, 132.8, 132.2, 130.4, 130.2, 129.9, 128.7, 128.3, 127.7, 127.6, 127.5, 126.9, 126.7, 126.1, 125.8, 125.6, 52.2, 44.5, 43.2, 23.1; IR (neat): 3057, 3024, 2947, 1724, 1433, 1215; HRMS (APCI) calcd for $C_{27}H_{23}O_2$ (M+H)$^+$ 379.16926. found 379.16952; HPLC (ODH, 0.5% isopropanol in hexane, 1.0 mL/min, 1 mg/mL, 30 min, UV 254 nm) retention times of 8.6 min (major) and 9.6 min (minor), >99% ee.

(R)-1-(naphthalen-2-yl)-2,2-diphenylcyclopropanecarboxylic acid

To a round-bottom flask at room temperature was added (R)-methyl 1-(naphthalen-2-yl)-2,2-diphenylcyclopropanecarboxylate (18.5 mmol, 7.0 g, 1.0 equiv) in dry DMSO (50 mL). $^t$-BuOK (41.0 mmol, 4.6 g, 2.2 equiv) was added in several portions over 30 minutes under argon. The reaction was monitored by TLC technique until the starting material was consumed completely. The reaction mixture was cooled with ice bath and acidified by saturated ammonium chloride aqueous (15 mL), followed by a slow addition of 1 N HCl (40 mL) with vigorous stirring until the pH value reached 3-4. Sticky solid precipitate was collected by filtration, washed with water (3×5 mL), dissolved in ethyl acetate (150 mL), washed with brine (3×10 mL), dried over anhydrous $MgSO_4$, and concentrated in vacuo. The crude material was purified using flash column chromatography eluting with a 4:1 mixture of hexanes/ethyl acetate to provide the desired product as a white solid (4.1 g, 61% yield. mp: 195-196° C.; $[\alpha]^{20}_D$ −361.7° (c=1.0, $CHCl_3$); $^1H$ NMR (400 MHz; $CDCl_3$) δ 7.80-7.76 (m, 3H), 7.65-7.59 (m, 3H), 7.53-7.46 (m, 3H), 7.42-7.34 (m, 3H), 7.11-7.09 (m, 2H), 7.0-6.9 (m, 3H), 2.73 (d, J=5.2 Hz, 1H), 2.65 (d, J=5.2 Hz, 1H); $^{13}C$ NMR (100 MHz, $CDCl_3$) δ 177.4, 141.5, 139.1, 133.1, 132.7, 132.3, 130.3, 130.1, 129.8, 128.6, 128.4, 127.7, 127.6, 127.5, 126.9, 126.7, 126.2, 125.8, 125.7, 42.7, 23.4; IR (neat): 3058, 1687, 1448, 1300; HRMS (APCI) calcd for $C_{26}H_{21}O_2$ (M+H)$^+$ 365.15361. found 365.15349; HPLC (to improve the separation, the product was converted to the corresponding methyl ester prepared using dimethylsulfate/KOH in tetrahydrofuran under reflux), HPLC (ODH, 0.5% isopropanol in hexane, 1.0 mL/min, 1 mg/mL, 30 min, UV 254 nm) retention times of 8.6 min (major) and 9.6 min (minor), >99% ee.

Dirhodium Tetrakis[(R)-1-(naphthalen-2-yl)-2,2-diphenylcyclopropanecarboxylate]

A solution of sodium rhodium carbonate [Na$_4$Rh$_2$(CO$_3$)$_4$]·2.5H$_2$O (599.6 mg, 1.0 equiv.) and (R)-1-(naphthalen-2-yl)-2,2-diphenylcyclopropanecarboxylic acid (3.0 g, 8.0 equiv.) in 60 mL distilled water was refluxed for 2 days under argon, and then the solution was extracted with dichloromethane (3×100 mL), organic extracts were combined, washed with saturated sodium bicarbonate (3×10 mL), 10% sodium hydroxide (3×10 mL), brine (3×10 mL), dried over anhydrous MgSO$_4$, and concentrated in vacuo. The crude material was purified using flash column chromatography eluting with a 50:1 mixture of toluene and acetonitrile to provide the desired catalyst as a green solid (989 mg, 58% yield). mp: 249-251° C.; [α]$^{20}_D$ 91.2° (c=0.02, CHCl$_3$); $^1$H NMR (400 MHz, CDCl$_3$): δ 7.70-7.67 (m, 8H), 7.54 (s, 4H), 7.43-7.29 (m, 32H), 7.24-7.21 (m, 4H), 7.10 (d, J=8.4 Hz, 4H), 6.92-6.85 (m, 12H), 6.75-6.65 (m, 12H), 2.48 (d, J=4.8 Hz, 4H), 2.02 (d, J=4.8 Hz, 4H). $^{13}$C NMR (100 MHz, CDCl$_3$) δ 188.9, 142.6, 140.9, 134.5, 132.6, 132.1, 130.9, 129.8, 129.0, 128.2, 128.1, 127.7, 127.6, 127.4, 127.3, 126.2, 126.1, 125.7, 125.4, 125.3, 46.6, 43.1, 23.5; IR (neat): 3056, 3023, 1579, 1389, 1348, 908, 744, 755, 704; HRMS (ESI) calcd for C$_{104}$H$_{76}$O$_8$Cl (M+Cl)$^+$ 1693.33443. found 1693.33556.

General Procedure for Catalyzed Cyclopropanation

To a 25 mL flame-dried round-bottom flask, kept under a dry atmosphere of argon, was added alkene (2.0 mmol, 5.0 equiv.), dry and degassed CH$_2$Cl$_2$ (1.0 mL) and then Rh$_2$(R-BTPCP)$_4$ (7.0 mg, 0.01 equiv.). The diazo compound (0.4 mmol, 1.0 equiv.), dissolved in dry and degassed CH$_2$Cl$_2$ (2 mL), was then added to the former solution drop-wise over 1 hour at room temperature. The mixture was allowed to stir for at least 30 min after the addition; when the diazo compound was fully consumed by TLC analysis, the reaction mixture was concentrated in vacuo. The crude residue was analyzed by $^1$H NMR and purified by flash column chromatography (hexanes/ethyl acetate) to afford the cyclopropane.

(1R,2R)-methyl 2-phenyl-1-((E)-styryl)cyclopropanecarboxylate (10)

This compound was prepared according to the general procedure for Rh2(R-BTPCP)4-catalyzed cyclopropanation. Using (E)-methyl 2-diazo-4-phenylbut-3-enoate 9 (0.4 mmol, 80.8 mg, 1.0 equiv.) and styrene 6 (2.0 mmol, 208 mg, 5.0 equiv.). The crude residue was analyzed by $^1$H NMR and purified by flash column chromatography (hexanes/ethyl acetate=50/1) to afford 10 as a white solid (95.3 mg, 86% yield). $^1$H NMR (400 MHz, CDCl$_3$): δ 7.25-7.21 (m, 4H), 7.19-7.13 (m, 6H), 6.35 (d, J=16.2 Hz, 1H), 6.14 (d, J=16.2 Hz, 1H), 3.77 (s, 3H), 3.04-2.99 (m, 1H), 2.03 (dd, J=9.2, 5.0 Hz, 1H), 1.88 (dd, J=7.3, 5.0 Hz, 1H); $^{13}$C NMR (100 MHz, CDCl$_3$) δ 174.1, 137.0, 135.5, 133.0, 129.1, 128.3, 127.9, 127.3, 126.7, 126.2, 124.0, 52.4, 34.9, 33.2, 18.6; HPLC (OJH, 1.5% isopropanol in hexane, 1.0 mL/min, 1 mg/mL, 30 min, UV 254 nm) retention times of 15.1 min (major) and 19.9 min (minor), 91% ee.

General Procedure for Rh2(R-BTPCP)4-Catalyzed Cyclopropanation/Cope Rearrangement To a 25 mL flame-dried round-bottom flask, kept under a dry atmosphere of argon, was added diene (2 mmol, 5.0 equiv.), dry and degassed CH$_2$Cl$_2$ (1.0 mL) and Rh$_2$(R-BTPCP)$_4$ (7.0 mg, 0.01 equiv.). The given diazo compound (0.4 mmol, 1.0 equiv.), dissolved in dry and degassed CH$_2$Cl$_2$ (2 mL), was then added to the former solution drop-wise over 1 hour at −40° C. The mixture was allowed to stir to room temperature overnight, and was concentrated in vacuo. The crude residue was analyzed by 1H NMR and purified by flash column chromatography (hexanes/ethyl acetate) to afford the desired 1,4-cycloheptadiene.

(3R,4S)-methyl 3,4-diphenylcyclohepta-1,5-dienecarboxylate (20a)

This compound was prepared according to the general procedure for Rh$_2$(R-BTPCP)$_4$-catalyzed cyclopropanation/Cope rearrangement. Using (E)-methyl 2-diazo-4-phenylbut-3-enoate 9 (0.4 mmol, 80.8 mg, 1.0 equiv.) and (E)-buta-1,3-dien-1-ylbenzene 19a (2.0 mmol, 260 mg, 5.0 equiv.). The crude residue was analyzed by $^1$H NMR and purified by flash column chromatography (hexanes/ethyl acetate=50/1) to afford 20a as a colorless oil (68.3 mg, 56% yield). $^1$H NMR (400 MHz, CDCl$_3$): δ 7.23-7.12 (m, 7H), 6.90-6.88 (m, 2H), 6.82-6.80 (m, 2H), 6.01-5.95 (m, 1H), 5.78 (ddd, J=11.4, 5.6, 2.7 Hz, 1H), 4.42 (s, 1H), 3.89 (s, 1H), 3.78 (s, 3H), 3.55-3.39 (m, 2H); $^{13}$C NMR (100 MHz, CDCl$_3$) δ 167.7, 144.5, 140.5, 139.8, 133.1, 132.3, 129.8, 129.1, 127.8, 127.5, 126.7, 126.6, 126.3, 52.0, 50.1, 49.6, 25.7; HPLC (S,S-Whelk, 1.5% isopropanol in hexane, 0.7 mL/min, 1 mg/mL, 30 min, UV 254 nm) retention times of 14.1 min (minor) and 15.8 min (major), 87% ee.

(3R,4S)-methyl 3-phenyl-4-(4-(trifluoromethyl)phenyl)cyclohepta-1,5-dienecarboxylate (20b)

This compound was prepared according to the general procedure for Rh$_2$(R-BTPCP)$_4$-catalyzed cyclopropanation/Cope rearrangement. Using (E)-methyl 2-diazo-4-phenylbut-3-enoate 9 (0.4 mmol, 80.8 mg, 1.0 equiv.) and (E)-1-(buta-1,3-dien-1-yl)-4-(trifluoromethyl)benzene 19b (2.0 mmol, 396 mg, 5.0 equiv.). The crude residue was analyzed by $^1$H NMR and purified by flash column chromatography (hexanes/ethyl acetate=50/1) to afford 20b as a colorless oil (105.2 mg, 71% yield). R$_f$=0.53 (hexanes/ethyl acetate=8/1); [α]$^{20}_D$ −60.7° (c=3.57, CHCl$_3$); $^1$H NMR (400 MHz, CDCl$_3$): δ 7.40 (d, J=8.2 Hz, 2H), 7.26-7.19 (m, 3H), 7.08 (dd, J=6.7, 2.7 Hz, 1H), 6.89-6.86 (m, 4H), 6.03-5.97 (m, 1H), 5.72 (ddd, J=11.4, 5.6, 2.9, 1H), 4.44 (s, 1H), 3.91-3.89 (m, 1H), 3.77 (s, 3H), 3.56-3.49 (m, 1H), 3.44-3.37 (m, 1H); $^{13}$C NMR (100 MHz, CDCl$_3$) δ 167.5, 143.9, 143.6, 140.0, 132.7, 132.0, 130.1, 129.4, 129.1, 128.9, 128.8, 128.6, 128.5, 128.0, 126.9, 125.6, 124.4, 124.3, 122.9, 52.0, 50.0, 49.2, 25.7; IR (neat): 3026, 2952, 1712, 1325; HRMS (APCI) calcd for C22H21F3O2 (M+H)$^+$ 373.14153. found 373.14045; HPLC (OJH, 1.0% isopropanol in hexane, 1.0 mL/min, 1 mg/mL, 30 min, UV 254 nm) retention times of 6.2 min (minor) and 7.7 min (major), 91% ee.

(3R,4S)-methyl 4-(4-methoxyphenyl)-3-phenylcyclohepta-1,5-dienecarboxylate (20c)

This compound was prepared according to the general procedure for Rh$_2$(R-BTPCP)$_4$-catalyzed cyclopropanation/Cope rearrangement. Using (E)-methyl 2-diazo-4-phenylbut-3-enoate 9 (0.4 mmol, 80.8 mg, 1.0 equiv.) and (E)-1-(buta-1,3-dien-1-yl)-4-methoxybenzene 19c (2.0 mmol, 320 mg, 5.0 equiv.). The crude residue was analyzed by $^1$H NMR and purified by flash column chromatography (hexanes/ethyl acetate=50/1) to afford 20c as a colorless oil (79.6 mg, 60% yield). R$_f$=0.51 (hexanes/ethyl acetate=8/1); [α]$^{20}_D$ −2.1° (c=3.01, MeOH); $^1$H NMR (400 MHz, CDCl$_3$): δ 7.27-7.21 (m, 3H), 7.11 (dd, J=6.7, 2.8 Hz, 1H), 6.90 (dd, J=6.7, 2.8 Hz, 1H), 6.71 (s, 4H), 5.95-5.94 (m, 1H), 5.74 (ddd, J=11.4, 5.6, 2.7 Hz, 1H), 4.39 (s. 1H), 3.79 (s. 3H), 3.77 (s, 3H), 3.52-3.46 (m, 1H), 3.42-3.37 (m, 1H); $^{13}$C NMR (100 MHz, CDCl$_3$) δ 167.7, 158.4, 144.7, 140.8, 133.4, 132.4, 131.8, 130.8, 129.0, 127.8, 126.7, 125.9, 112.9, 55.1, 52.0, 49.7, 49.4, 25.7; IR (neat): 3010, 2950, 2359, 1708, 1509; HRMS (APCI) calcd for C22H24O3 (M+H)+ 335.16471. found 335.16378; HPLC (S,S-Whelk, 1.5% isopropanol in hexane, 0.7 mL/min, 1 mg/mL, 30 min, UV 254 nm) retention times of 23.9 min (minor) and 26.0 min (major), 89% ee.

Procedure for $Rh_2(R\text{-BTPCP})_4$-Catalyzed Combined C—H Cope/Retro Cope Rearrangement (R,E)-methyl 2-((S)-4-methyl-1,2-dihydronaphthalen-2-yl)-4-phenylbut-3-enoate (22)

To a 25 mL flame-dried round-bottom flask, kept under a dry atmosphere of argon, was added 4-methyl-1,2-dihydronaphthalene (2 mmol, 5.0 equiv.), dry and degassed $CH_2Cl_2$ (1.0 mL) and $Rh_2(R\text{-BTPCP})_4$ (7.0 mg, 0.01 equiv.). The given diazo compound (0.4 mmol, 1.0 equiv.), dissolved in dry and degassed $CH_2Cl_2$ (2 mL), was then added to the former solution drop-wise over 1 hour at room temperature. The mixture was allowed to stir for overnight, and was then concentrated in vacuo. The crude residue was analyzed by $^1H$ NMR and purified by flash column chromatography (hexanes/ethyl acetate=50/1) to afford the desired product 22 as a colorless oil (117.3 mg, 92% yield). The NMR spectral data are consistent with previously published results. $R_f$=0.60 (hexanes/ethyl acetate=8/1); $^1H$ NMR (400 MHz, $CDCl_3$): δ 7.36-7.07 (m, 9H), 6.42 (d, J=15.9 Hz, 1H), 6.14 (dd, J=15.9, 9.8 Hz, 1H), 5.73 (d, J=3.1 Hz, 1H), 3.70 (s, 3H), 3.11 (t, J=9.5 Hz, 1H), 2.89-2.83 (m, 2H), 2.74-2.70 (m, 1H), 2.07 (s, 3H); $^{13}C$ NMR (100 MHz, $CDCl_3$) δ 173.9, 136.9, 135.5, 134.6, 133.9, 128.8, 128.0, 127.9, 127.4, 126.8, 126.6, 126.5, 126.3, 123.3, 53.4, 52.1, 36.3, 31.9, 19.6; HPLC (OD, 2.0% isopropanol in hexane, 0.8 mL/min, 1 mg/mL, 30 min, UV 254 nm) retention times of 8.9 min (minor) and 10.5 min (major), 98% ee.

What is claimed:

1. A dirhodium catalyst with a carboxylic acid ligand covalently bonded to a cyclopropyl ring substituted with a carbocyclyl, aryl, or heterocyclyl.

2. A composition comprising a compound of the following formula,

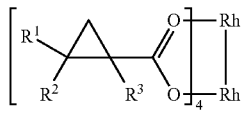

or salts thereof wherein,
$R^1$ is carbocyclyl, aryl, or heterocyclyl wherein $R^1$ is optionally substituted with one or more, the same or different, $R^4$;
$R^2$ is hydrogen, alkyl, halogen, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^4$;
$R^3$ is hydrogen, alkyl, halogen, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^4$;
$R^4$ is alkyl, halogen, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$;
$R^5$ is alkyl, halogen, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$; and
$R^6$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

3. The composition of, claim 2, wherein $R^1$ is an aryl or an aromatic heterocyclyl.

4. The composition of claim 2, wherein $R^1$ is a phenyl optionally substituted with one or more $R^4$.

5. The composition of claim 2, wherein $R^1$ is a phenyl optionally substituted with one or more halogen, alkyl, or alkoxy.

6. The composition of claim 2, wherein $R^2$ is carbocyclyl, aryl, or heterocyclyl.

7. The composition of claim 2, wherein $R^2$ is an aryl or an aromatic heterocyclyl.

8. The composition of claim 2, wherein $R^2$ is a phenyl optionally substituted with one or more $R^4$.

9. The composition of claim 2, wherein $R^2$ is a phenyl optionally substituted with one or more halogen, alkyl, or alkoxy.

10. The composition of claim 2, wherein $R^3$ is carbocyclyl, aryl, or heterocyclyl.

11. The composition of claim 2, wherein $R^3$ is an aryl or an aromatic heterocyclyl.

12. The composition of claim 2, wherein $R^3$ is a phenyl optionally substituted with one or more $R^4$.

13. The composition of claim 2, wherein $R^3$ is a phenyl optionally substituted with one or more halogen, alkyl, or alkoxy.

14. The composition of claim 2, wherein $R^3$ is a phenyl substituted with a halogen.

15. The composition of claim 2, wherein $R^3$ is a phenyl substituted with a halogen in the ortho or para position.

16. A composition comprising a compound,

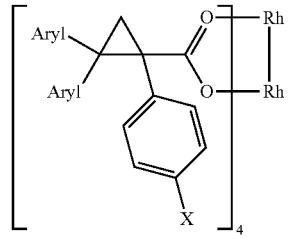

wherein X is an electron withdrawing group.

17. The composition of claim 16, wherein X is a halogen.

18. A composition comprising a compound

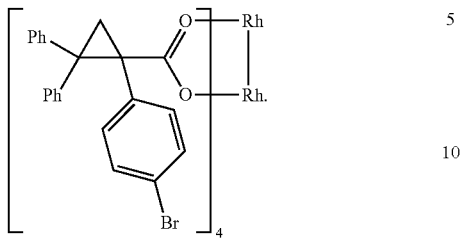

19. A method of making a synthetic compound comprising mixing
   a) a diazo compound,
   b) a compound with a carbon hydrogen bond, and
   c) a compound comprising a compound as in claim 2,
      under conditions such that a synthetic compound is formed comprising a carbon to carbon bond between the diazo compound and the compound with a carbon hydrogen bond.

20. A method of making a synthetic compound comprising mixing
   a) a diazo compound,
   b) a compound with a nitrogen hydrogen bond, and
   c) a compound comprising a compound as in claim 1,
      under conditions such that a synthetic compound is formed comprising a carbon to nitrogen bond between the diazo compound and the compound with a nitrogen hydrogen bond.

* * * * *